US008021667B2

(12) United States Patent
McKenzie et al.

(10) Patent No.: US 8,021,667 B2
(45) Date of Patent: *Sep. 20, 2011

(54) COMPOSITIONS FOR IMMUNOTHERAPY AND USES THEREOF

(75) Inventors: Ian F. C. McKenzie, Brunswick (AU); Vasso Apostolopoulos, St. Albans (AU); Geoffrey A. Pietersz, Greensborough (AU)

(73) Assignee: MacFarlane Burnet Institute for Medical Research and Public Health Ltd, Melbourne (AU)

( * ) Notice: Subject to any disclaimer, the term of this patent is extended or adjusted under 35 U.S.C. 154(b) by 1158 days.

This patent is subject to a terminal disclaimer.

(21) Appl. No.: 11/561,300

(22) Filed: Nov. 17, 2006

(65) Prior Publication Data

US 2007/0092531 A1 Apr. 26, 2007

Related U.S. Application Data

(63) Continuation of application No. 09/163,089, filed on Sep. 29, 1998, now abandoned, which is a continuation-in-part of application No. 08/833,807, filed on Apr. 9, 1997, now Pat. No. 5,989,552, which is a continuation of application No. 08/340,711, filed on Nov. 16, 1994, now abandoned, said application No. 09/163,089.

(60) Provisional application No. 60/060,594, filed on Sep. 29, 1997.

(51) Int. Cl.
*A61K 39/00* (2006.01)
*A61K 39/12* (2006.01)
*A61K 39/02* (2006.01)
*A61K 39/015* (2006.01)

(52) U.S. Cl. ............... 424/185.1; 424/204.1; 424/234.1; 424/272.1; 424/277.1; 530/350

(58) Field of Classification Search ........................ None
See application file for complete search history.

(56) References Cited

U.S. PATENT DOCUMENTS

| 4,720,386 | A | 1/1988 | McCollester |
| 5,047,227 | A | 9/1991 | Rodwell et al. |
| 5,229,289 | A | 7/1993 | Kjeldsen et al. |
| 5,432,260 | A | 7/1995 | Stahl |
| 5,820,872 | A | 10/1998 | Edelson et al. |
| 6,017,527 | A | 1/2000 | Maraskovsky et al. |
| 2007/0071765 | A1 | 3/2007 | McKenzie et al. |

FOREIGN PATENT DOCUMENTS

| AU | A-41876/89 | 3/1990 |
| EP | 0 308 147 A1 | 3/1989 |
| EP | 0 326 111 A2 | 8/1989 |
| EP | 0 659 768 A2 | 6/1995 |
| FR | 2 279 422 | 2/1976 |
| JP | 46-016913 | 5/1971 |
| JP | 61-112023 | 5/1986 |
| JP | 1-233219 | 9/1989 |
| JP | 5-246860 | 9/1993 |
| WO | WO 89/08711 A1 | 9/1989 |
| WO | WO 90/05142 A1 | 5/1990 |
| WO | WO 92/11033 A1 | 7/1992 |
| WO | WO 93/06858 A1 | 4/1993 |
| WO | WO 93/14195 A1 | 7/1993 |
| WO | WO 93/17712 A2 | 9/1993 |
| WO | WO 94/06916 A1 | 3/1994 |
| WO | WO 94/13312 A1 | 6/1994 |
| WO | WO 95/18145 A1 | 7/1995 |
| WO | WO 98/13378 A1 | 4/1998 |

OTHER PUBLICATIONS

Abbas, A.K., et al.,"Class I MHC-Associated Antigen Presentation," in *Cellular and Molecular Immunology*, Wonsiewicz, M.J., eds., W.B. Saunders Co., Philadelphia, PA, pp. 131 (1991).
Ada in *Fundamentals of Immunology*, $2^{nd}$ Ed., Chapter 36, William, P., ed., Lippincott Williams and Wilkins, Philadelphia, PA, pp. 985-1032 (1989).
Aizawa, K., et al., "Antitumor Effect of a Baker's Yeast Mannan-Mitomycin C Conjugate Against Mouse Hepatoma, MH134, In Vivo and In Vitro," *Int. J. Immunopharmacol.* 11:191-195, Elsevier Science Ltd. (1989).
Apostolopoulos, V., et al., "Production of anti-breast cancer monoclonal antibodies using a glutathione-S-transferase-MUC1 bacterial fusion protein," *Br. J. Cancer* 67:713-720, Nature Publishing Group (1993).
Apostolopoulos, V., et al., "Oxidative/reductive conjugation of mannan to antigen selects for $T_1$ or $T_2$ immune responses," *Proc. Natl. Acad. Sci. U.S.A.* 92:10128-10132, National Academy of Sciences (1995).
Apostolopoulos, V., et al., "Cell-mediated immune responses to MUC1 fusion protein coupled to mannan," *Vaccine* 14:930-938, Elsevier Science Ltd. (1996).
Apostolopoulos, et al., "Adoptive Immunotherapy Using Macrophage/Dendritic Cells Stimulated with M-FP In Vitro Induce CTL In Vivo," Australian Society of Immunology, Abstract P85 (1996).
Apostolopoulos, V., et al., "MUC1 cross-reactive Galα(1,3)Gal antibodies in humans switch immune responses from cellular to humoral," *Nat. Med.* 4:315-320, Nature Publishing Company (Mar. 1998).
Apostolopoulos, V., et al., "Peptide mimics of a tumor antigen induce functional cytotoxic T cells," *Nat Biotechnol.* 16:276-280, Nature America Publishing (Mar. 1998). Apostolopoulos, V., et al., "Aldehyde-mannan antigen complexes target the MHC class I antigen-presentation pathway," *Eur. J. Immunol* 30:1714-1723, VCH Verlagsgesellschaft (2000).
Barnd, D.L., et al., "Specific, major histocompatibility complex-unrestricted recognition of tumor-associated mucins by human cytotoxic T cells," *Proc. Natl. Acad. Sci. U.S.A.* 86:7159-7163, National Academy of Sciences (1989).
Davis, W.C., et al., "Use of the Mannan Receptor to Selectively Target Vaccine Antigens for Processing and Antigen Presentation through the MHC Class I and Class II Pathways," *Ann. N.Y. Acad. Sci.* 969:119-125, New York Academy of Sciences (2002).
Denton, G., et al., "Induction of antibody responses to breast carcinoma associated mucins using synthetic peptide constructs as immunogens," *Cancer Lett.* 70:143-150, Elsevier Science Ireland (1993).

(Continued)

*Primary Examiner* — Robert A Zeman
(74) *Attorney, Agent, or Firm* — Sterne, Kessler, Goldstein & Fox P.L.L.C.

(57) ABSTRACT

The present invention relates to an immunogenic composition comprising a conjugate between an antigen and an oxidized mannan comprising mannose units and aldehyde groups, and a pharmaceutically acceptable carrier.

9 Claims, 14 Drawing Sheets

OTHER PUBLICATIONS

Devine, P.L., et al., "The Breast Tumor-associated Epitope Defined by Monoclonal Antibody 3E1.2 Is an O-linked Mucin Carbohydrate Containing N-Glycolylneuraminic Acid," *Cancer Res. 51*:5826-5836, American Association for Cancer Research (1991).

Ding, L., et al., "Immunogenicity of synthetic peptides related to the core peptide sequence encoded by the human MUC1 mucin gene: effect of immunization on the growth of murine mammary adenocarcinoma cells transfected with the human MUC1 gene," *Cancer Immunol. Immunother. 36*:9-17, Springer Verlag (1993).

Ellis, R.W., "New Technologies for Making Vaccines," in *Vaccines*, Plotkin et al. Eds., W. B. Saunders Co., Philadelphia, PA, pp. 568-575 (1988).

Fontenot, J.D., et al., "Biophysical Characterization of One-, Two-, and Three—Tandem Repeats of Human Mucin (muc-1) Protein Core," *Cancer Res. 53*:5386-5394, American Association for Cancer Research (1993).

Hanisch, F.-G., et al., "Structures of Neutral O-Linked Polylactosaminoglycans on Human Skim Milk Mucins," *J. Biol. Chem. 264*:872-883, American Society for Biochemistry and Molecular Biology (1989).

Hudecz, F. and Price, M.R., "Monoclonal antibody binding to peptide epitopes conjugated to synthetic branched chain polypeptide carriers. Influence of the carrier upon antibody recognition," *J. Immunol. Methods 147*:201-210, North-Holland Pub. Co. (1992).

Jerome, K.R., et al., "Expression of Tumor-associated Epitopes on Epstein-Barr Virus-immortalized B-Cells and Burkitt's Lymphomas Transfected with Epithelial Mucin Complementary DNA," *Cancer Res. 52*:5985-5990, American Association for Cancer Research (1992).

Karanikas, V., et al., "Antibody and T Cell Responses of Patients with Adenocarcinoma Immunized with Mannan-MUC1 Fusion Protein," *J. Clin. Invest. 100*:2783-2792, American Society for Clinical Investigation (1997).

Lalani, E.-N., et al., "Expression of the Gene Coding for a Human Mucin in Mouse Mammary Tumor Cells Can Affect Their Tumorigenicity," *J. Biol. Chem. 266*:15420-15426, American Society for Biochemistry and Molecular Biology (1991).

Langsdale, T., "A vaccine cure for breast cancer within sight?," *Inpharma Weekly 915*:3-4, ADIS Press, Ltd. (1993).

Lew, D.B., et al., "A Mannose Receptor Mediates Mannosyl-rich Glycoprotein-induced Mitogenesis in Bovine Airway Smooth Muscle Cells," *J. Clin. Invest. 94*:1855-1863, American Society for Clinical Investigation 1994.

Lofthouse, S.A., et al., "Induction of $T_1$ (cytotoxic lymphocyte) and/or $T_2$ (antibody) responses to a mucin-1 tumour antigen," *Vaccine 15*:1586-1593, Elsevier Science Ltd. (Oct. 1997).

McCool, D.J., et al., "The T84 human colonic adenocarcinoma cell line produces mucin in culture and releases it in response to various secretagogues," *Biochem. J. 267*:491-500, Portland Press (1990).

Mitchell, M.S., T-Cell-Mediated Immunity to Carcinoembryonic Antigen in Humans: an Example of "Swimming Upstream," *J. Natl. Cancer Inst. 87*:949-951, Oxford University Press (1995).

Mukhopadhyay, A., and Staphl, P., "Bee Venom Phospholipase $A_2$ Is Recognized by the Macrophage Mannose Receptor," *Arch. Biochem. Biophys. 324*:78-84, Academic Press (1995).

Murata, J.-I., et al., Synthesis of muramyl dipeptide analogue-glucomannan conjugate and its stimulation activity against macrophage-like cells, *Carbohydrate Polymers 29*:111-118, Elsevier Science Ltd. (1996).

Nurmukhamedov, T.A., et al., "Conjugates of Active Staphylotoxin Fractions for Induction of Intense Antibody Formation," *Immunologiya 4*:61-63, Allerton Press (1991) see English abstract at p. 63.

Okawa, Y., et al., "Production of anti-peptide specific antibody in mice following immunization with peptides conjugated to mannan," *J. Immunol. Methods 149*:127-131, North-Holland Pub. Co. (1992).

Robbins, J.C., et al., "Synthetic glycopeptide substrates for receptor-mediated endocytosis by macrophages," *Proc. Natl. Acad. Sci. U.S.A. 78*:7294-7298, National Academy of Sciences (1981).

Rossi, G. and Himmelhoch, S., "Binding of Mannosylated Ferritin to Chicken Bone Marrow Macrophages," *Immunobiology 165*:46-62, Gustav Fischer Verlag (1983).

Schlom, J., et al., "Strategies for the development of recombinant vaccines for the immunotherapy of breast cancer," *Breast Cancer Res. Treat. 38*:27-39, Kluwer Academic (1996).

Stahl, P.D. and Ezekowitz, R.A.B., "The mannose receptor is a pattern recognition receptor involved in host defense," *Curr. Opin. Immunol. 10*:50-55, Current Biology (Feb. 1998).

Takata, I., et al., "L-Fucose, D-Mannose, L-Galactose, and Their BSA Conjugates Stimulate Macrophage Migration," *J. Leukoc. Biol. 41*:248-256, Wiley-Liss (1987).

Taylor-Papadimitriou, J. and Finn, O.J., "Biology, biochemistry and immunology of carcinoma-associated mucins," *Immunol. Today 18*:105-107, Elsevier Science Publishers (Mar. 1997).

Tsang, K.Y. et al., "Generation of Human Cytotoxic T Cells Specific for Human Carcinoembryonic Antigen Epitopes From Patients Immunized With Recombinant Vaccinia-CEA Vaccine," *J. Natl. Cancer Inst. 87*:982-990, Oxford University Press (1995).

Venisse, A., et al., "Mannosylated lipoarabinomannan interacts with phagocytes," *Eur. J. Biochem. 231*:440-447, Blackwell Science Ltd. (1995).

Abbas, A.K. et al., eds., Basic Immunology—Functions and disorders of the Immune System, $2^{nd}$ edition, Updated Edition 2006-2007, p. 53, Saunders, Elsevier, Philadelphia.

Sheng, K.C. et al., "Mannan derivatives induce phenotypic and functional maturation of mouse dendritic cells," *Immunology 118*(3): 372-383 (Jul. 2006) Blackwell Publishing Ltd., Oxford, England.

Bakker, ABH et al., "Generation of Antimelanoma Cytotoxic T Lymphocytes from Healthy Donors after Presentation of Melanoma-associated Antigen-derived Epitopes by Dendritic Cells in Vitro," Cancer Res. 55:5330-5334 (Nov. 1995), American Association of Cancer Research, Philadelphia, PA.

Celluzzi, CM et al., "Peptide-pulsed dendritic cells induce antigen-specific CTL-mediated protective tumor immunity," J. Exp. Med. 183:283-287 (Jan. 1996), Rockefeller University Press, New York, NY.

Engering, AJ et al., "The mannose receptor functions as a high capacity and broad specificity antigen receptor in human dendritic cells," Eur J Immunol 27(9): 2417-2425 (Sep. 1997), Wiley Verlag, Weinheim, Germany.

Jerome, KR et al., "Cytotoxic T-Lymphocytes Derived from Patients with Breast Adenocarcinoma Recognize an Epitope Present on the Protein Core of a Mucin Molecule Preferentially Expressed by Malignant Cells," Cancer Res. 51: 2908-2916 (Jun. 1991), American Association of Cancer Research, Philadelphia, PA.

Kusunoki, K. et al., Derivation of Immune Tolerance from Glycoprotein Antigens and Antigen-presenting Function of Dendritic Cells, Ann. Meet. Jap. Soc. Immunol. 26: 370 (1996), abstract 3P5-21, Japanese Society of Immunology, Tokyo, Japan.

Lanzavecchia, A., "Mechanisms of antigen uptake for presentation," Curr Opin Immunol 8(3): 348-354 (Jun. 1996), Elsevier, Ltd., New York, NY.

Mayordomo, JI et al., "Bone marrow-derived dendritic cells pulsed with synthetic tumour peptides elicit protective and therapeutic antitumour immunity," Nat Med 1(12): 1297-1302 (Dec. 1995), Nature Publishing Group.

Paglia, P., Murine dendritic cells loaded in vitro with soluble protein prime cytotoxic T lymphocytes against tumor antigen in vivo, J. Exp. Med. 183: 317-322 (Jan. 1996), Rockefeller University Press, New York, NY.

Tan, MC et al., "Mannose receptor-mediated uptake of antigens strongly enhances HLA class II-restricted antigen presentation by cultured dendritic cells," Eur J Immunol, 27(9): 2426-2435 (Sep. 1997), Wiley Verlag, Weinheim, Germany.

Office action from U.S. Appl. No. 11/561,204, mailed Feb. 26, 2010.

SEQUENCE LISTING

```
<160> NUMBER OF SEQ ID NOS: 9

<210> SEQ ID NO 1
<211> LENGTH: 20
<212> TYPE: PRT
<213> ORGANISM: Homo sapiens

<400> SEQUENCE: 1

Ser Ala Pro Asp Thr Arg Pro Ala Pro Gly Ser Thr Ala Pro Pro Ala
 1               5                  10                  15

His Gly Val Thr
            20

<210> SEQ ID NO 2
<211> LENGTH: 23
<212> TYPE: PRT
<213> ORGANISM: Homo sapiens

<400> SEQUENCE: 2

Pro Thr Thr Thr Pro Ile Ser Thr Thr Thr Met Val Thr Pro Thr Pro
 1               5                  10                  15

Thr Pro Thr Gly Thr Gln Thr
            20

<210> SEQ ID NO 3
<211> LENGTH: 17
<212> TYPE: PRT
<213> ORGANISM: Homo sapiens

<400> SEQUENCE: 3

His Ser Thr Pro Ser Phe Thr Ser Ser Ile Thr Thr Thr Glu Thr Thr
 1               5                  10                  15

Ser

<210> SEQ ID NO 4
<211> LENGTH: 16
<212> TYPE: PRT
<213> ORGANISM: Homo sapiens

<400> SEQUENCE: 4
```

-continued

```
Thr Ser Ser Ala Ser Thr Gly His Ala Thr Pro Leu Pro Val Thr Asp
 1               5                  10                  15

<210> SEQ ID NO 5
<211> LENGTH: 8
<212> TYPE: PRT
<213> ORGANISM: Homo sapiens

<400> SEQUENCE: 5

Pro Thr Thr Ser Thr Thr Ser Ala
 1               5

<210> SEQ ID NO 6
<211> LENGTH: 23
<212> TYPE: PRT
<213> ORGANISM: Homo sapiens

<400> SEQUENCE: 6

Thr Thr Ala Ala Pro Pro Thr Pro Pro Ala Thr Thr Pro Ala Pro Pro
 1               5                  10                  15

Ser Ser Ser Ala Pro Pro Glu
            20

<210> SEQ ID NO 7
<211> LENGTH: 5
<212> TYPE: PRT
<213> ORGANISM: Homo sapiens

<400> SEQUENCE: 7

Ala Pro Asp Thr Arg
 1               5

<210> SEQ ID NO 8
<211> LENGTH: 9
<212> TYPE: PRT
<213> ORGANISM: Homo sapiens

<400> SEQUENCE: 8

Ala Pro Asp Thr Arg Pro Ala Pro Gly
 1               5

<210> SEQ ID NO 9
<211> LENGTH: 12
<212> TYPE: PRT
<213> ORGANISM: Homo sapiens

<400> SEQUENCE: 9

Asp Thr Arg Pro Ala Pro Gly Ser Thr Ala Pro Pro
 1               5                  10
```

US 8,021,667 B2

COMPOSITIONS FOR IMMUNOTHERAPY AND USES THEREOF

CROSS-REFERENCE TO RELATED APPLICATIONS

The present application is a continuation of U.S. patent application Ser. No. 09/163,089, filed Sep. 29, 1998, for "Compositions For Immunotherapy and Uses Thereof", which is a continuation-in-part of U.S. patent application Ser. No. 08/833,807, filed Apr. 9, 1997, for "Antigen Carbohydrate Compounds and Their Use in Immunotherapy", which is a continuation of U.S. patent application Ser. No. 08/340,711 for "Antigen Carbohydrate Compounds and Their Use in Immunotherapy", filed Nov. 16, 1994. U.S. patent application Ser. Nos. 09/163,089, 08/833,807 and 08/340,711 are incorporated herein by this reference in their entirety. U.S. patent application Ser. No. 09/163,089 also claims benefit to U.S. Provisional Application No. 60/060,594, filed Sep. 29, 1997, for "Compositions for Immunotherapy and Uses Thereof", incorporated herein by reference in its entirety.

FIELD OF THE INVENTION

The present invention relates to a product and process for regulating the activity of T cells using a carbohydrate compound. The product of the present invention particularly concerns a mannose receptor-bearing cell and an oxidized mannose linked to an antigen, the product being capable of enhancing MHC class I antigen presentation.

BACKGROUND OF THE INVENTION

Cancer is a major cause of death and severe trauma in modern society. Cancer afflicts the young, old, males, females and peoples of all races may contract cancer, although cancer in children is relatively rare, perhaps with the exception of childhood leukemia. In western society, cancer of the colon and lung cancer are major diseases. In women, breast cancer is the most common form of cancer.

Many cancers are accompanied by overproduction of human mucin. Mucins are heavily glycosylated proteins (greater than about 100 kilodalton (kD) which are produced by many epithelial cells and tumors (Gendler et al., *J. Biol. Chem*, 263:12820-12823, 1988). Mucins found on cancer cells are different in some respects to those on normal epithelial cells, in that some mucins have a deficiency in their carbohydrate coat which leaves the protein core exposed (Harisch et al., *J. Biol. Chem.*, 264:872-883, 1989). There are seven forms of known human mucin designated MUC1, MUC2, MUC3, MUC4, MUC5, MUC6 and MUC7 (Marjolijn et al., *J. Biol. Chem.*, 265:5573-5578, 1990; Crocker et al., *Br. J. Cancer,* 55:651-652, 1987; Apostolopoulos et al., *Crit. Rev. Immunol.*, 14:293-309, 1994; and Bobek et al., *J. Biol. Chem.*, 268:20563-20569, 1993). MUC1 is the most ubiquitous. The various mucins all have very similar properties, that is, they are transmembrane glycoproteins, all having a variable number of repeated amino acid sequences, which have a high content of serine, threonine and proline. Overproduction of aberrantly glycosylated mucins (either non-glycosylated or a deficiency in glycosylation) is characteristic of tumors of the breast, ovary, pancreas, colon, lungs, prostate and other tumors of secretory tissue. The copy DNA (cDNA) sequences of the respective protein cores of the human mucins MUC1 to MUC7 have been cloned and characterized and have been found to contain highly repetitive central portions of varying numbers of repeats of particularly amino acid motifs (known as VNTR's). By way of example, MUC1 consists of unique amino and carboxyl terminal sequences separated by a highly repetitive central portion containing forty to eighty tandemly arranged copies or repeats of a twenty amino acid motif. The VNTR's of MUC1 through MUC7 are set forth below:

| MUC1 | VNTR- | SAPDTRPAPGSTAPPAHGVT | (SEQ ID NO: 1) |
|---|---|---|---|
| MUC2 | VNTR- | PTTTPISTTTMVTPTPTGTQT | (SEQ ID NO: 2) |
| MUC3 | VNTR- | HSTPSFTSSITTTETTS | (SEQ ID NO: 3) |
| MUC4 | VNTR- | TSSASTGHATPLPVTD | (SEQ ID NO: 4) |
| MUC5 | VNTR- | PTTSTTSA (494 base pair insert - eight amino acid tandem repeat) | |
| MUC6 | VNTR- | 169 amino acid repeat unit | (SEQ ID NO: 5) |
| MUC7 | VNTR- | TTAAPPTPPATTPAPPSSSAPPE | (SEQ ID NO: 6) |

The repeated subunit of MUC6 comprises 169 amino acids, although at this time the amino acid sequence of this repeat unit has not been fully characterized. The MUC7 sequence has recently been published (Bobek et al., ibid.).

Finn and colleagues have demonstrated that in the lymph nodes of patients with breast cancer (Barnd et al., *Proc. Natl. Acad. Sci USA,* 86:7159-7163, 1989; and Jerome et al., in *Cell. Immunity and Immunotherapy of Cancer*, pp. 321-328, 1990), cancer of the pancreas, ovary and other tumors, cytotoxic lymphocytes are present which react with human mucin. Antibodies to the MUC1 peptide can block the activity of these cytotoxic T lymphocytes on MUC1 and target cells (Barnd et al., ibid.; and Jerome et al., ibid.). Recently, cytotoxic lymphocytes to a murine lung cancer have also been described (Mandelboimo et al., *Nature,* 369:67-71, 1994).

The surgery associated with tumor removal is traumatic to the patient, often disfiguring, and costly. Established chemotherapeutic and radiation procedures for tumor treatment which may be carried out in place of, or in conjunction with, surgical procedures are often debilitating and associated with severe side-effects. There is accordingly an urgent need for immunoregulatory compositions and methods for the prevention/treatment of tumors.

There is an urgent need for new compositions and methods for the treatment of cancer. Similarly, there is a pressing need for alternative compositions and methods for the treatment of other disease states such as type I allergies, malaria, HIV, dental caries, flu, cholera, foot and mouth disease, meningitis, *Leishmania* infection, whooping cough, rabies, *Streptococcus* infection, respiratory infection, measles, Lyme disease, tuberculosis, bacterial meningitis, shingles, *rubella*, hepatitis, herpes, hepatitis A, polio, venereal disease/trachoma, hepatitis B, common cold, cervical cancer, meningitis/pneumonitis, chicken pox, small pox and pneumonia/PUO.

SUMMARY OF THE INVENTION

The present invention provides an immunoregulatory composition that is capable of regulating a T lymphocyte (T cell) response in an animal, thereby treating or alleviating the occurrence of disease. The present invention is advantageous because it regulates T cell responses by delivering an antigen to the MHC class I pathway for presentation by class I molecules, thereby inducing cytotoxic T lymphocytes and T1 (i.e., TH1) cytokine production, e.g., IL-2, IL-12 and gamma interferon. The invention is particularly advantageous in that it regulates T cell responses by increasing the uptake of an antigen:carbohydrate polymer conjugate of the present invention by inducing receptors for mannose on cells capable of stimulating T cells reactive to the antigen of the conjugate. In addition, the invention is particularly advantageous in that it enables an antigen, for example a mucin:carbohydrate polymer conjugate of the present invention, to be administered to an animal in such a manner that binding of the antigen, e.g., mucin, by naturally occurring antibodies directed against or crossreactive with the antigen in the animal is avoided. Moreover, an immunoregulatory composition of the present invention possesses the advantage of being substantially non-toxic upon administration to animals, and as a consequence the compositions are well tolerated by animals.

One embodiment of the present invention includes an immunoregulatory composition comprising isolated mannose receptor-bearing cells and a conjugate comprising an antigen and mannose including fully oxidized mannose and/or partially reduced mannose having aldehydes. Preferred antigens include tumor, viral, fungal, protozoal or bacterial antigens. Preferred oxidized mannose comprises a carbohydrate polymer with aldehydes.

Another embodiment of the present invention includes a composition comprising an immunoregulatory mannose receptor-bearing cell population, the population can be derived by culturing mannose receptor-bearing cells under conditions effective to produce the immunoregulatory mannose receptor-bearing cell population, the conditions comprising an antigen delivery medium. A preferred antigen delivery medium comprises a conjugate comprising an antigen and mannose including oxidized mannose and/or partially reduced mannose having aldehydes.

Yet another embodiment of the present invention includes an immunoregulatory mannose receptor-bearing cell population, in which the immunoregulatory mannose receptor-bearing cell population can be derived by a method comprising:
(a) culturing mannose receptor-bearing cells in vitro with one or more biological response modifiers to produce an enhanced mannose receptor-bearing cell population; and
(b) incubating the enhanced mannose receptor-bearing cell population with a conjugate comprising an antigen and mannose including oxidized mannose and/or partially reduced mannose having aldehydes, to obtain the immunoregulatory mannose receptor-bearing cell population. Preferred biological response modifiers include cytokines and vitamins.

The present invention also includes an antigen delivery vehicle, comprising an isolated mannose receptor-bearing cell and a conjugate comprising antigen and a carbohydrate polymer comprising mannose including fully oxidized mannose and/or partially reduced mannose having aldehydes. Preferred antigen includes mucin. The present invention also includes a method for obtaining a population comprising immunoregulatory mannose receptor-bearing cells, the method comprising culturing a population of cells enriched for mannose receptor-bearing cells under conditions effective to obtain immunoregulatory mannose receptor-bearing cells, the conditions comprising an antigen delivery medium. Preferably, the method includes incubating the population of cells enriched for mannose receptor-bearing cells in the presence of one or more biological response modifier prior to the step of culturing.

Another embodiment of the present invention includes a method to induce an immune response comprising administering to a recipient animal an effective amount of an immunoregulatory composition comprising mannose receptor bearing cells and a conjugate comprising an antigen and mannose including fully oxidized mannose and/or partially reduced mannose having aldehydes.

The invention also includes a method to induce an immune response to an antigen, comprising contacting an isolated mannose receptor-bearing cell with a conjugate comprising antigen and mannose including fully oxidized mannose and/or partially reduced mannose having aldehydes, and administering the contacted cell to an animal.

Also included in the present invention is a method for delivering an antigen to an animal by administering to an animal a mannose receptor-bearing cell that has been contacted with a conjugate comprising an antigen and mannose including fully oxidized mannose and/or partially reduced mannose having aldehydes, in which the mannose receptor-bearing cell is capable of presenting the antigen to a T cell in such a manner that a response is elicited from the T cell.

Yet another embodiment of the present invention is a compound comprising an antigen conjugated to a carbohydrate polymer comprising partially reduced carbohydrate having aldehyde groups.

DETAILED DESCRIPTION OF THE INVENTION

Figure 1:
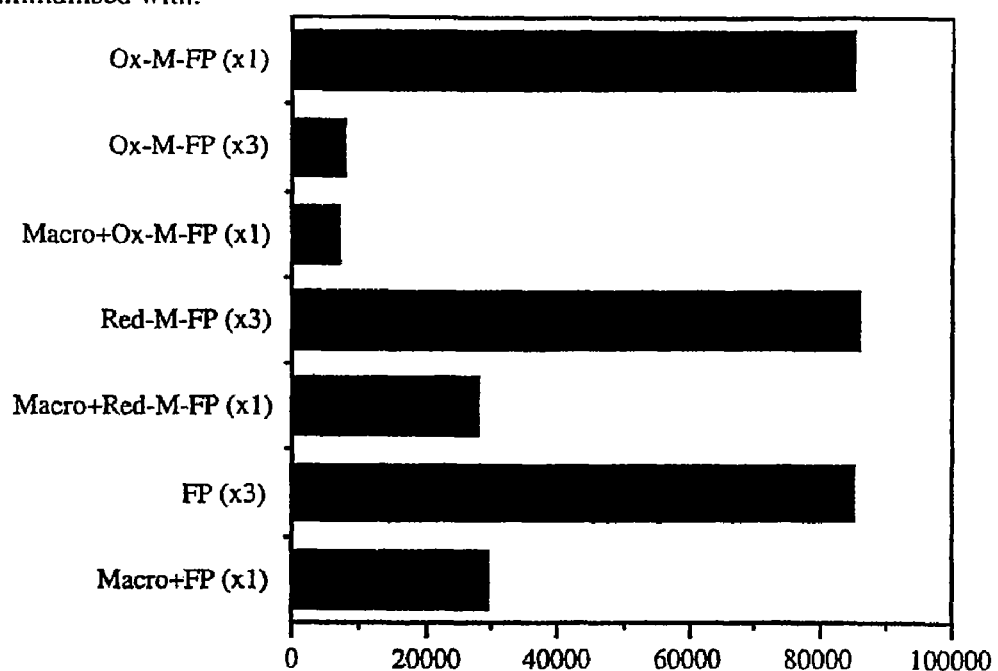
FIG. 1 illustrates CTLp frequencies obtained by a single in vitro immunization compared to three in vivo immunizations using peritoneal exudate cells pulsed with different forms of mannose polymer.

The present invention provides a product and process for treating or alleviating the occurrence of disease in an animal susceptible to immunoregulation. In particular, the product includes an immunoregulatory composition comprising carbohydrate receptor-bearing cells, and a conjugate comprising an antigen and oxidized carbohydrate.

One embodiment of the present invention is an immunoregulatory composition comprising isolated carbohydrate receptor-bearing cells and a conjugate comprising an antigen and oxidized carbohydrate. As used herein, the term "oxidized carbohydrate" can refer to a completely (i.e., fully) oxidized carbohydrate or a partially reduced carbohydrate having aldehydes (described in detail below). Another embodiment of the present invention is receptor-bearing cells contacted with a conjugate comprising an antigen and oxidized carbohydrate. According to the present invention, reference to a composition comprising "carbohydrate receptor-bearing cells and a conjugate comprising an antigen and oxidized carbohydrate" or "carbohydrate receptor-bearing cells contacted with a conjugate comprising an antigen and oxidized carbohydrate" can encompass one or more of: (1) a mixture of conjugate and receptor-bearing cells wherein the conjugate is not bound to the cells; (2) a mixture of conjugate and receptor-bearing cells wherein the conjugate is bound to the cells, but not yet internalized; (3) receptor-bearing cells wherein the conjugate has been internalized; (4) receptor-bearing cells wherein the conjugate has been internalized and processed; and/or (5) receptor-bearing cells wherein the conjugate has been internalized, processed and presented. It is to be noted that the term "a" or "an" entity refers to one or more of that entity; for example, a compound refers to one or more compounds. As such, the terms "a" (or "an"), "one or more" and "at least one" can be used interchangeably herein. The term "isolated" refers to an entity, such as a cell, polypeptide or peptide, that has been removed from its natural milieu. As such, "isolated" does not reflect the extent to which the entity has been purified. As used herein, a "carbohydrate receptor-bearing cell" refers to any type of cell that contains a receptor (i.e., protein) that specifically binds to carbohydrate on the surface of the cell or that is capable of expressing a carbohydrate receptor. Carbohydrate receptors as used herein refer to those carbohydrate receptors known to those of skill in the art. It is to be noted that carbohydrate receptor-bearing cells can be part of a population of cells containing varying concentrations of carbohydrate receptor-bearing cells. Thus, a population of carbohydrate receptor-bearing cells includes a population of cells that includes at least one carbohydrate receptor-bearing cell. Alternatively, a population of carbohydrate receptor-bearing cells can comprise a pure population of carbohydrate receptor-bearing cells (i.e., 100% carbohydrate receptor-bearing cells). Preferably, a population of carbohydrate receptor-bearing cells comprises at least about 25%, more preferably at least about 50%, more preferably at least about 75%, even more preferably at least about 80%, even more preferably at least about 85%, even more preferably at least about 90% and even more preferably at least about 95% carbohydrate receptor-bearing cells. It is within the knowledge of one of skill in the art to note that the relative purity of a population of carbohydrate receptor bearing cells can be dependent upon the source of the carbohydrate receptor-bearing cells. As used herein, an "enriched population of carbohydrate receptor-bearing cells" refers to a population of cells that has been treated in such a manner that non-carbohydrate receptor-bearing cells (i.e., cells having, or being capable of expressing, carbohydrate receptor) have been removed from the population. As used herein, an "enhanced carbohydrate receptor-bearing cell population" refers to a population of cells that has been treated in such a manner that the number of cells bearing carbohydrate receptor, and/or the number of carbohydrate receptors on a cell, increases compared with cells in the population prior to the treatment. Carbohydrate receptor bearing cells can be enriched in a population of cells from, for example, blood, bone marrow, lymph node or bronchial lavage, using methods standard in the art, including, but not limited to, panning, leukophoresis or growth enriching techniques. Methods to enhance a population of carbohydrate receptor-bearing cells are described in detail herein.

Suitable carbohydrate receptor-bearing cells for use with the present invention include cells that have been isolated from an animal or cells that have been adapted to tissue culture and are grown in vitro. As used herein, the term "in vitro" refers to methods performed outside of an animal. The term "ex vivo" refers to methods performed on a portion (e.g., tissue, cells and fluids) of an animal (i.e., donor animal), outside of the animal, with the intent to return the portion to an animal (i.e., recipient animal). The recipient animal need not be the same animal as the donor animal. Preferred carbohydrate receptor-bearing cells of the present invention are derived from bone marrow, peripheral blood leukocytes, alveolar lung macrophages, stem cells, tumor cells and/or stromal cells. Cells can be isolated from an animal using standard methods known in the art depending upon the source of the cells. More preferred carbohydrate receptor-bearing cells include cells that are enriched for antigen presenting cells (APC). Suitable antigen presenting cells include cells capable of presenting an antigen to a T cell, thereby eliciting a T cell response. A portion of an immune response is regulated by presentation of antigen by major histocompatibility complexes (MHCs). MHCs bind to peptide fragments derived from antigens to form complexes that are recognized by T cell receptors on the surface of T cells, giving rise to the phenomenon of MHC-restricted T cell recognition. A "T cell response" refers to the reaction of a T cell to antigen presented by the MHC and peptide complex. A response by T cell can include activation of the T cell such as with a naive T cell, or stimulation of a T cell such as with a T cell that is already activated. A "cell mediated immune response" refers to an immune response that involves the activation and/or stimulation of a T cell. According to the present invention, a conjugate or composition of the present invention can elicit a T cell response by activating and/or stimulating T cells, in particular antigen-specific T cells. Preferred antigen presenting cells include dendritic cells, macrophages, monocytes and B lymphocytes (B cells), with macrophage and monocyte cells being more preferred. Even more preferred carbohydrate receptor-bearing cells include mannose receptor-bearing cells, i.e. cells having mannose receptors. As used herein, "receptor-bearing" and receptor positive cells are intended to be used interchangeably. Even more preferred carbohydrate receptor-bearing cells of the present invention include cells that are enriched for cells that bind specifically to an antibody including F4/80, anti-MAC-1 antibody, anti-mannose receptor antibody, NLDC-145, anti-CD14 antibody, anti-CD11b antibody, anti-CD11C antibody, anti-CD68 antibody, anti-CD80 antibody or anti-CD86 antibody.

Preferably, a carbohydrate receptor-bearing cell of the present invention originates from an animal that is the intended recipient of the immunoregulatory composition or an animal that is MHC matched to the intended recipient, such as from an unrelated donor or a relative of the animal, preferably a sibling of an animal. A preferred carbohydrate receptor-bearing cell is obtained from an animal that is the intended recipient of the immunoregulatory composition of the present invention.

In one embodiment, carbohydrate receptor-bearing cells of the present invention include carbohydrate receptor-bearing cells that have been contacted with a compound capable of inducing the expression of receptors for carbohydrate on cells capable of expressing carbohydrate receptors. Suitable compounds useful for inducing the expression of carbohydrate receptors include biological response modifiers, such as cytokines. Preferred biological response modifiers of the present invention include any compound capable of inducing the expression of carbohydrate receptors on monocytes, macrophages and/or dendritic cells. More preferred biological response modifiers include, but are not limited to, cytokines and vitamins. Preferred cytokines useful for increasing the number of carbohydrate receptors on the surface of a cell include, but are not limited to, granulocyte macrophage colony stimulating factor (GM-CSF), interleukin-3 (IL-3), interleukin-4 (IL-4), interferon gamma, Flt-3 ligand; granulocyte colony stimulating factor (G-CSF); interleukin-12 (IL-12), tumor necrosis factor alpha (TNF-a), macrophage colony stimulating factor (M-CSF), interleukin-3 (IL-3), interleukin-4 (IL-4) and/or interleukin-6 (IL-6), with GM-CSF and IL-3 being more preferred. A preferred vitamin for use with the present invention includes, but is not limited to, vitamin D.

According to the present invention, carbohydrate receptor-bearing cells can be contacted with a biological response modifier prior to or after the carbohydrate receptor-bearing cells are removed from an animal. As such, a biological response modifier can be administered to an animal under conditions suitable for inducing carbohydrate receptors on cells in vivo.

In a preferred embodiment, carbohydrate receptor-bearing cells of the present invention include a population of cells containing monocytes, macrophages and/or dendritic cells that have been contacted with a formulation comprising GM-CSF, IL-3, IL-4, TNF gamma and/or vitamin D.

One embodiment of the present invention is a method for obtaining a cell population comprising immunoregulatory carbohydrate receptor-bearing cells, the method comprising culturing a population of cells enriched for carbohydrate receptor-bearing cells under conditions effective to obtain immunoregulatory carbohydrate receptor-bearing cells, in which the conditions comprise an antigen delivery medium. An antigen delivery medium includes a conjugate of the present invention, preferably a conjugate comprising an antigen and oxidized carbohydrate. Additional components of an antigen delivery medium include suitable cell culture medium such as that disclosed herein in the Examples and those known to one of skill in the art. Methods to culture a population of cells enriched for carbohydrate receptor-bearing cells are disclosed herein in the Examples. Preferably, the culturing step is performed from about 1 day to about 12 days, more preferably from about 3 days to about 10 days, and even more preferably from about 5 days to about 7 days, with 5 days being even more preferred.

The present invention also includes an immunoregulatory carbohydrate receptor-bearing cell population that can be derived by the method comprising: (a) culturing carbohydrate receptor-bearing cells in vitro with one or more biological response modifiers to produce an enhanced carbohydrate receptor-bearing cell population; and (b) incubating the enhanced carbohydrate receptor-bearing cell population with a conjugate comprising an antigen and oxidized carbohydrate to obtain an immunoregulatory carbohydrate receptor-bearing cell population. Preferably, the step of culturing is performed from about 1 hour to about 6 hours, more preferably from about 2 hours to about 4 hours and even more preferably for about 3 hours. A preferred carbohydrate receptor-bearing cell population derived by the present method include mannose receptor-bearing cells.

According to the present invention, an antigen includes a polypeptide or a peptide. Antigens of the present invention initiates a series of events culminating in an immune response, cellular or humoral. In particular, antigens of the present invention include those that are presented to T cells in the context of MHC. Suitable antigens for use with the present invention include polypeptides and peptides. Polypeptides comprising an antigen may be produced according to well known procedures such as peptide synthesis, protein purification, or expression of polypeptides in host cells. Peptide synthesis may be employed for polypeptides containing up to about a hundred amino acids (for example, five repeated subunits of MUC1). Generally, for polypeptide containing about twenty or more amino acids, the preferred means of production is recombinant expression in a host cell, preferably a prokaryotic host cell, and more preferably a bacterial host cell. However, as discussed earlier, eukaryotic systems may also be used. Procedures for expression of recombinant proteins in host cells are well established, see, for example, Sambrook et al., *Molecular Cloning: A Laboratory Manual*, Cold Spring Harbor Press, Cold Spring Harbor, 1989.

According to the present invention, a peptide of the present invention is an isolated peptide. An isolated peptide refers to a peptide that is not in its natural milieu. An isolated peptide of the present invention can be obtained from its natural source, produced by proteolysis of a full-length protein or larger protein fragment, produced using recombinant DNA technology or synthesized using standard chemical peptide synthesis methods.

Insofar as the present invention is concerned, the antigen can be an autoantigen or an antigenic peptide derived from a virus, microorganism or plant or an amino acid subunit of at least five amino acids in length of an autoantigen or an antigenic peptide derived from a virus, microorganism or plant. The antigen of the present invention can also consist of more than one, five or more amino acid subunits (as mentioned above) linked together. These linked subunits may be from the same or different origins within the bounds described above. An antigenic peptide of the present invention is capable of binding to an MHC molecule.

Examples of the antigens suitable for use in a composition of the present invention include: tumor antigens including, but not limited to CEA, p53, Her2/neu, ErB2, melan A, MAGE antigens, nm23, BRACA1, BRACA2; pollens, hepatitis C virus (HIV) core, E1, E2 and NS2 proteins; *Plasmodium falicparum* circumsporozoite protein; HIV-gp120/160 envelope glycoprotein; *streptococcus* surface protein Ag; influenza nucleoprotein; hemagglutinin-neuraminidase surface infection; TcpA pilin subunit; VP1 protein; LMCV nucleoprotein; *Leishmania* major surface glycoprotein (gp63); *Bordetella pertussis* surface protein; rabies virus G protein; *Streptococcus* M protein; respiratory syncytial virus (RSV) F or G proteins; Epstein Barr virus (EBV) gp340 or nucleoantigen 3A, hemagglutinin, *Borrelia burgdorferi* outer surface protein (Osp) A, *Mycobacterium tuberculosis* 38 kDa lipoprotein or Ag85, *Neisseria meningitides* class 1 outer protein, *Varicella zoster* virus IE62 and gpI, *Rubella* virus capsid protein, Hepatitis B virus pre S1 ag, Herpes simplex virus type I glycoprotein G or gp D or CP27, Murray valley encephalitis virus E glycoprotein, Hepatitis A virus VP1, polio virus capsid protein VP1, VP2 and VP3, *chlamydia trachomatis* surface protein, Hepatitis B virus envelope Ag pre S2, Human rhinovirus (HRV) capsid, *papillomavirus* peptides from oncogene E6 and E7, *Listeria* surface protein, *Varicella* virus envelope protein, *Vaccinia* virus envelope protein, *Brucella* surface protein, a combination of one or more of said antigens, an amino acid subunit of said antigens comprising five or more amino acids in length or combinations of one or more of such subunits.

The antigens of the present invention can also consist of whole cells or sub-cellular fractions thereof. Such cells or sub-cellular fractions thereof may be derived from any tumor type or other source. Examples of cancer types from which the whole cells or sub-cellular fractions may be derived are breast, lung, pancreas and colon cancer and melanoma. Some further examples of specific antigens obtained from tumors are melanoma specific antigen (for example, the MAGE series antigen), carcino embryonic antigen (CEA) from colon and other cancers or indeed antigens extracted from any tumor.

This invention includes any one or more of the antigens listed above, and in particular includes any one or more of the human mucins MUC1 through MUC7 which, as mentioned above, all comprise highly repetitive central portions of repeated amino acid sequences which are high in serine, threonine and proline. In particular, the compositions of this invention may comprise a human mucin polypeptide (containing a variable number of repeats associated with normal allelic variation), or may comprise one or more of the repeated sequences of human mucin, preferably two to eighty, more preferably two to twenty and even more preferably two to ten repeated subunits of human mucin. The human mucin and subunits thereof are preferably non-glycosylated or aberrantly glycosylated so as to provoke an immune response to the mucins found on cancer cells which have a deficiency in their carbohydrate coat which leaves the protein core exposed. The use of human mucin MUC1 is particularly preferred although it is to be clearly understood that the invention extends to the use of any antigen and especially to the use of the human mucins MUC1 through MUC7. For the purpose of convenience, the term MUC will hereafter be used to refer to any of the human mucins MUC1 through MUC7 and repeated subunits thereof. While only the human mucins will be dealt with hereafter, it must be kept in mind that this invention equally relates to any other antigen as mentioned previously.

Fragments of MUC may also be conjugated to a carbohydrate polymer. These fragments can comprise any portion of a molecule MUC that is capable of being conjugated to a carbohydrate. Fragments of a MUC molecule include fragments of the naturally-occurring sequence of a MUC molecule and/or a sequence derived from a MUC molecule but modified to improve binding of a MUC molecule to a MHC class I molecule. Methods to mimic a MUC molecules include methods known to those in the art, such as peptide synthesis or recombinant DNA techniques. Preferred fragments of a MUC molecule comprise peptides of a MUC molecule. A preferred peptide of a MUC molecule is from about five to about twenty amino acids. Preferred fragments of a MUC molecule comprise non-VNTR or VNTR regions. More preferred fragments of a MUC molecule include peptides having an amino acid sequence including APDTR (SEQ ID NO:7), APDTRPAPG (SEQ ID NO:8), DTRPAPGSTAPP (SEQ ID NO:9), and the like. For convenience of description these fragments are also included with the definition MUC. Similarly, other antigen fragments comprising at least five amino acids may be conjugated to a carbohydrate polymer.

A specified antigen of the present invention may form part of a fusion protein in order to facilitate expression and purification on production of the fusion protein in recombinant host cells. The non-antigen portion of the fusion protein would generally represent the N-terminal region of the fusion polypeptide with the carboxy terminal sequences comprising antigen sequences. Fusion proteins may be selected from glutathione-S-transferase, β-galactosidase, or any other protein or part thereof, particularly those which enable affinity purification utilizing the binding or other affinity characteristics of the protein to purify the resultant fusion protein. The protein may also be fused to the C-terminal or N-terminal of the carrier protein. The nature of the fusion protein will depend upon the vector system in which fusion proteins are produced. An example of a bacterial expression vector is pGEX which on subcloning on a gene of interest into this vector produces a fusion protein consisting of glutathione-S-transferase with the protein of interest. Examples of other vector systems which give rise to fusion proteins with a protein of interest are described in Sambrook et al., ibid., which is incorporated herein in its entirety by reference. These can be included or cleaved; if included they could a have a "carrier" function.

The protein or fusion protein may be expressed in a number of prokaryotic (*E. coli* or β-*subtilis*) or eukaryotic (baculovirus, CHO cells, Cos cells or yeast) expression systems. In some of these systems, for example, baculovirus or yeast, by introducing glycosylation motifs into the protein or fusion protein, the mannose rich glycosylation may be adequate; negating the need for chemically linking with mannose rich carbohydrate polymers. These novel fusion proteins may be used with or without mild periodate oxidation.

In one embodiment, an antigen of the present invention is conjugated to a carbohydrate polymer. The number of repeated monomer units in the carbohydrate polymer is not important but generally carbohydrate polymers would comprise at least twenty monomer units, preferably in excess of one hundred monomer units, more preferably in excess of one thousand monomer units, and still more preferably in excess of ten thousand monomer units or more. Carbohydrate polymers may be a mixture of polysaccharide chains of varying molecular weights. The carbohydrate portion of a composition of the present invention can comprise any carbohydrate polymer, for example, polymers including glucose, galactose, mannose, xylose, arabinose, fucose, glucosamine, galactosamine, rhamnose, 6-0-methyl-Dgalactose, 2-0-acetyl-β-D-xylose, N-acetyl-glucosamine, iduronate, gluuronate, mannuronate, methyl galacturonate, a-D-galactopyranose-6-sulphate, fructose and a-abequose, conformation and configuration isomers thereof, or a carbohydrate formed of two or more different monomer units. A preferred carbohydrate polymer of the present invention comprises mannose. A more preferred carbohydrate polymer is a polymer of the carbohydrate mannose. An even more preferred carbohydrate polymer is a polymer of fully oxidized mannose and/or partially reduced mannose having aldehydes.

A preferred carbohydrate comprises an oxidized carbohydrate treated in such a manner that the carbohydrate is partially reduced. A more preferred carbohydrate comprises an oxidized carbohydrate treated in such a manner that aldehyde groups of the carbohydrate are substantially not reduced, and predominantly Schiff's bases are reduced. A suitable reagent for partially reducing a carbohydrate according to the present invention includes, but is not limited to, sodium cyanoborohydride. It is understood that other reagents suitable for partially reducing a carbohydrate according to the present invention will be apparent to those of skill in the art and are intended to be encompassed herein. Treatment of an oxidized carbohydrate with sodium cyanoborohydride, for example, retains aldehyde groups while reducing other groups, such as Schiff's bases. Without being bound by theory, the present inventors believe that exposed and/or free aldehyde groups of an oxidized carbohydrate according to the present invention are important for delivery of the carbohydrate and antigen conjugate of the present invention, possibly by altering uptake, release, or leakage of antigen from the endosomes or lysosomes into the cytoplasm. In a preferred embodiment, an oxidized carbohydrate comprises oxidized mannose units of a carbohydrate polymer substantially comprising free aldehydes. It is to be noted that a carbohydrate polymer of the present invention can include fully oxidized mannose or partially reduced mannan having aldehydes. Carbohydrates may be purified from natural sources or synthesized according to conventional procedures. Carbohydrates are available commercially from many suppliers.

Figure 14:
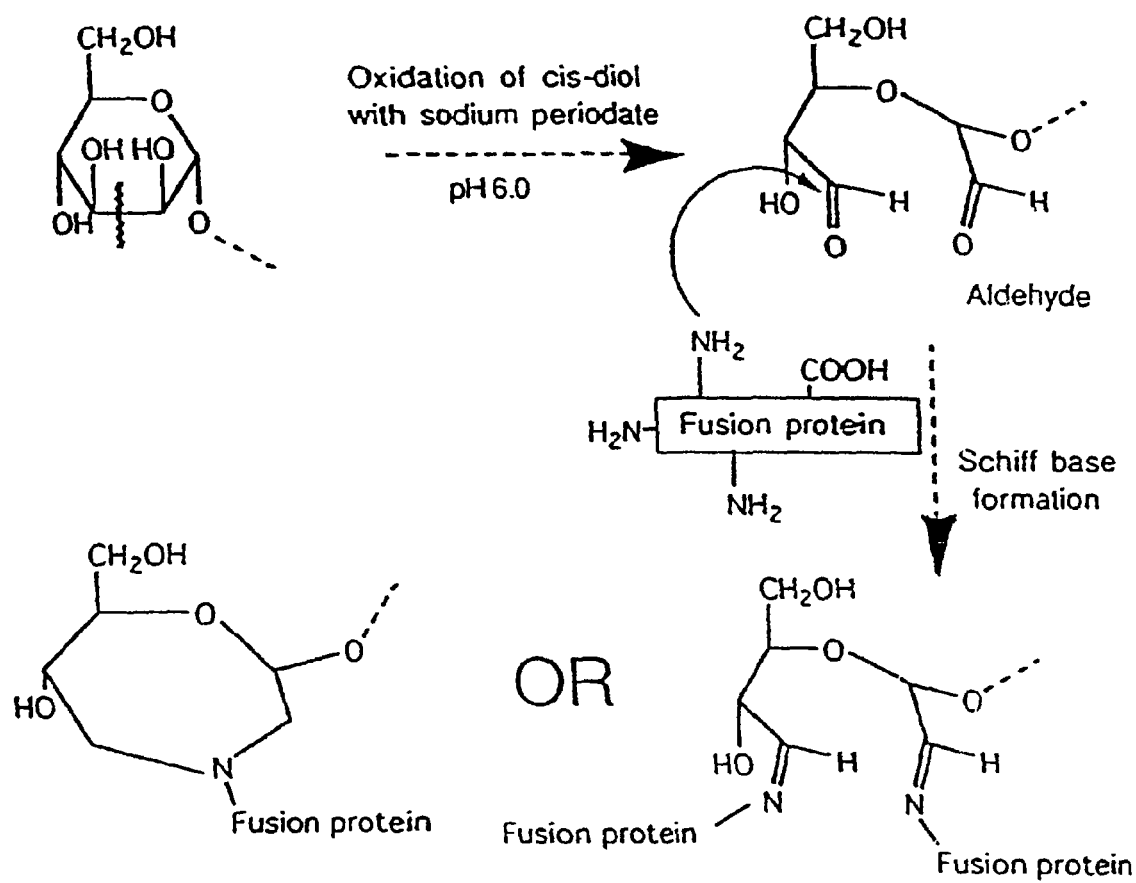
FIG. 14 illustrates coupling of MUC1 fusion protein to mannan.

Antigens may be conjugated to a carbohydrate polymer according to standard processes well known in the art of carbohydrate chemistry for the derivatization and reaction of polysaccharides and monosaccharides. Carbohydrates may be oxidized with conventional oxidizing reagents such as a periodate, for example sodium periodate, to give a polyaldehyde which is then directly reacted with the antigen (such as repeated subunits of MUC1) where amino functional groups on the protein chain (such as the e group of lysine) react with the aldehyde groups which form Schiff's bases (see FIG. 14). Polysaccharide chains may be first activated with cyanogen bromide and the activated polysaccharide then reacted with a diamine, followed by conjugation to the antigen to form a conjugate which may optionally then be oxidized. The carbohydrate and polypeptide may be derivatized with bifunctional agents in order to cross-link the carbohydrate and polypeptide. Commonly used cross-linking agents include 1,1-bis(diazoacetyl)-2-phenylethane, glutaraldehyde, N-hydroxysuccinimide esters, for example, esters with 4-azidosalicyclic acid, homobifunctional imidoesters including disuccinimidyl esters such as 3,3'-dithiobis(succinimidylpropionate), and bifunctional maleimides such as bis-Nmaleimido-1,8-octane. Derivatizing agents such as methyl-3[(p-azido-phenyl)dithio]propioimidate yield photoactivatable intermediates which are capable of forming cross-links in the presence of light. Oxidized carbohydrates may be reacted with hydrazine derivatives of antigens to give a conjugate. Alternatively, carbohydrates may be reacted with reagents such as carbonyl diimidazole, which after oxidation gives the desired conjugate. Such methods of conjugation and oxidation have been previously discussed, for example, in PCT Application No. PCT/AU94/00789 (WO 95/18145), filed Dec. 23, 1994, which is incorporated herein by reference in its entirety. It is to be understood that other methods of conjugation and oxidation of carbohydrates according to the present invention will be apparent to those of skill in the art and are intended to be encompassed herein.

The coupling of antigens to a carbohydrate involves converting any or all of the functional groups on the carbohydrate to reactive groups and thereafter reacting the reactive groups on the carbohydrate with reactive groups on the polypeptide. Carbohydrate polymers are replete with hydroxyl groups, and in some instances, carboxyl groups (such as in idruionate), ester groups (such as methylgalacturonate) and the like. These groups may be activated according to standard chemical procedures. For example, hydroxyl groups may be reacted with hydrogen halides, such as hydrogen iodide, hydrogen bromide and hydrogen chloride to give the reactive halogenated polysaccharide. Hydroxy groups may be activated with phosphorous trihalides, active metals (such as sodium ethoxide, aluminium isopropoxide and potassium tert-butoxide), or esterified (with groups such as tosyl chloride or acetic acid) to form reactive groups which can be then be reacted with reactive groups on the polypeptide to form one or more bonds. Other functional groups on carbohydrates apart from hydroxyl groups may be activated to give reactive groups according to well known procedures in the art.

In one preferred embodiment of the present invention, there is provided an immunoregulatory composition comprising a population of cells enriched for mannose receptor-bearing macrophage and/or monocyte cells, and a conjugate between a human mucin polypeptide, one or more repeated or non-repeated subunits thereof, or a fragment of the repeated or nonrepeated subunits, with a carbohydrate polymer comprising oxidized mannose. In particular, the immunoregulatory composition comprises a population of cells enriched for mannose receptor-bearing macrophage and/or monocyte cells that have been contacted with GM-CSF, IL-3, IL-4, TNF gamma and/or vitamin D prior to being combined with the conjugate.

Immunoregulatory compositions of the present invention can be formulated in a pharmaceutically acceptable carrier. Examples of such carriers include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the carrier can comprise dextrose, human serum albumin, preservatives, etc., to which sterile water or saline can be added prior to administration. Pharmaceutically acceptable carriers of the present invention can further comprise immunopotentiators, such as adjuvants or delivery vehicles. Adjuvants are typically substances that generally enhance the immune response of an animal to a specific antigen. Suitable adjuvants include those adjuvants that can be administered to animals, in particular humans. Preferred adjuvants for use with immunoregulatory composition of the present invention include, but are not limited to, aluminum-based salts; calcium-based salts; silica; gamma interferon; IL-12 and other commercially available adjuvants.

In another aspect, an immunoregulatory composition of the present invention is administered to a patient to protect against or treat the patient for various disease states. In particular, an immunoregulatory composition of the present invention is useful for treating or preventing the growth of abnormal cells. As used herein, an abnormal cell refers to a cell displaying abnormal biological function, such as abnormal growth, development or death. Abnormal cells of the present invention, preferably include cancer cells, cells infected with an infectious agent (i.e., a pathogen) and non-cancerous cells having abnormal proliferative growth (e.g., sarcoidosis, granulomatous disease or papillomas) and with cancer cells and infected cells. Cancer cell growth includes, but is not limited to, the growth of tumors of secretory tissues, such as tumors of the breast, colon, lung, pancreas, prostate, and the like.

Some other disease states which may be protected against in this manner include, but are not limited to, type I allergies, malaria, HIV, dental caries, flu, cholera, foot and mouth disease, meningitis, *Leishmania* infection, whooping cough, rabies, *Streptococcus* infection, respiratory infection, measles, Lyme disease, tuberculosis, bacterial meningitis, shingles, *rubella*, hepatitis, herpes, hepatitis A, polio, venereal disease/trachoma, hepatitis B, common cold, cervical cancer, meningitis/pneumonitis, chicken pox, small pox and pneumonia/PUO.

Animals may be immunized with an immunoregulatory composition of the present invention to protect against tumor formation of secretory tissues. Alternatively, animals suffering from tumors may be immunized with the immunoregulatory composition of the present invention as part of a therapeutic regimen for tumor treatment. By way of example, to protect women from breast cancer, women may be immunized with the immunoregulatory composition of the present invention pre- or post-puberty and may receive one or more injections, preferably an initial immunization, followed by one or more booster injections separated by several months to several years. In one immunization schedule, women may be immunized with the compositions of the invention and then receive a booster immunization at appropriate intervals. Further booster immunizations are then provided at regular intervals. The route of immunization is no different from conventional human vaccine administration. Accordingly, an immunoregulatory composition of the present invention may be administered subcutaneously, intramuscularly, orally, intravenously, and the like.

The amount of compositions of the present invention delivered to an animal is not critical or limiting. An effective amount of a composition of the invention is that which will stimulate an immune response against the antigen component. The amount of compositions delivered may vary according to the immune status of the animal (depending on whether the patient is immunosuppressed or immunostimulated), the judgement of attending physician or veterinarian whether the compound is used as a therapeutic to prevent or treat a disease state. A suitable single dose is a dose that is capable of protecting an animal from, or treating an animal with, a particular disease when administered one or more times over a suitable time period. For example, animals may receive from about $10^5$ to about $10^{13}$ cells in a composition of the present invention, more preferably from about $10^6$ to about $10^{12}$ and even more preferably from about $10^7$ to about $10^{11}$ in a composition of the present invention.

As described above, compositions of the present invention may be administered to animals in concert with an adjuvant, such as a cytokine or other compound that enhance an immune response. By way of example, such enhancing compounds which may be administered in concert with a composition of the present invention include one or more of GM-CSF, G-CSF, M-CSF, TNFa or β, interferon gamma or alpha, any of IL-1 through IL-18, or any other cytokine. The enhancing compound may be administered to an animal at the same time as a composition of the present invention, optionally as part of a multi-component administration form. Alternatively, the enhancing compound of and a composition of the present invention may be administered at different time intervals following administration of an immunoregulatory composition of the present invention.

In another aspect of this invention, there is provided a method for inducing an immune response against antigens which comprises administering to an animal an immunoregulatory composition of the present invention. Administration of an immunoregulatory composition of the present invention to an animal provokes a potentiated cellular response of activated T cells, in particular cytotoxic to cells reacting with the antigen component. By way of example, an animal may be immunized against tumors which express mucins or other tumor antigenic determinants. A potential benefit of this invention arises from the fact that animals may be protected against cancer prior to tumor growth, as a composition of the present invention may provoke a cellular immune response of cytotoxic T cells which kill tumor cells expressing mucin or other antigenic determinants. This invention is particularly applicable to the immunization against tumors of secretory tissue, such as adenocarcinomas, more particularly, tumors of the breast, ovary, pancreas, colon, lung, prostate and the like.

One embodiment of the present invention includes a method for inducing an immune response in an animal, the method comprising administering to an animal an effective amount of an immunoregulatory composition comprising mannose receptor-bearing cells and a conjugate comprising an antigen and oxidized mannose. An effective amount of an immunoregulatory composition of the present invention comprises an amount capable of preventing or treating a disease as described herein.

Animals for use with the present invention include, but are not limited to, humans, companion animals and food animals, with humans or monkeys being more preferred, and humans being most preferred.

Another embodiment of the present invention is a method to induce an immune response in an animal against cancer, the method comprising administering to an animal an effective amount of an immunoregulatory composition comprising carbohydrate receptor-bearing cells and a conjugate comprising an antigen and oxidized carbohydrate. A preferred carbohydrate for use with the present method is mannose. Any antigen disclosed herein is suitable for use with the present method. A preferred antigen comprises a mucin polypeptide.

A composition of the present invention may be administered as a part of the overall treatment for eradication of the cancer or alone. If administered as part of an overall treatment, a composition of the present invention can administered prior to, during or after another form of treatment. For example, a composition of the present invention may be administered to animals suffering from cancer either before or after surgery to remove cancerous cells. Similarly, a composition of the present invention can be administered before or after a chemotherapeutic or radiation regime following tumor excision. Preferably, a composition of the present invention is administered at a time when the immune system of an animal is intact such that a cell mediated immune response can be induced in the animal. As such, a composition of the present invention is not preferably administered following immune ablation treatment of an animal. When administering an immunoregulatory composition of the present invention to an animal having a tumor, preferably the composition is administered in or around the primary site of the tumor.

In a preferred embodiment, a method to induce an immune response comprises the steps of: (a) isolating a mannose receptor-bearing cell population from an animal; (b) contacting the cells with one or more biological response modifiers to produce an enhanced mannose receptor-bearing cell population; (c) combining the enhanced mannose receptor-bearing cell population with a conjugate of an antigen and oxidized mannose to produce an immunoregulatory mannose receptor-bearing cell population; and (d) administering the immunoregulatory mannose receptor-bearing cell population to an animal to induce an immune response. Preferred cytokines and vitamins for use with this embodiment are disclosed herein.

In a still further aspect, the invention relates to the use of a compound comprising a conjugate between the human mucin polypeptide, one or more repeated subunits thereof, or a fragment of said repeated subunits and a carbohydrate polymer in the treatment of adenocarcinoma, particularly breast cancer.

The invention described herein is not restricted to the human mucin MUC1. The invention clearly extends to the use of other mucins expressed by cancer cells, as well as to the use of other antigens which on coupling to polysaccharides, can be used to provoke cytotoxic T cell responses against tumor cells, which compounds may be used in vaccines to prevent tumor formation, as well as for the treatment of cancer, and/or the treatment or prophylaxis of other disease states as mentioned earlier. A variety of antigens corresponding to various diseases and conditions against which the elicitation of an immune response is desirable are well known in the art, such antigens being equally included within the scope of the present invention.

The present invention also includes a method for delivering an antigen of the present invention to an animal that has preexisting antibodies (i.e., natural antibodies) that bind to the antigen, such method resulting in elicitation of a cellular immune response to the antigen. One of the advantages of the method of the present invention is the ability to avoid the binding of conjugates by naturally occurring antibodies (i.e., natural antibodies) which may be capable of binding to the antigen of interest, thereby preferentially inducing an antibody response over a cellular immune response. For example, in the case of the antigen, mucin, humans have large quantities of circulating, naturally occurring antibodies that bind to the mucin peptide. The specificity of these naturally occurring antibodies is mostly derived against a galactose epitope, but these antibodies cross react with the mucin peptide. Thus, when a patient is immunized with the mannan:mucin conjugate, the antibodies presumably bind to the conjugate and prevent it from getting to the appropriate antigen presenting pathways to induce a cellular immune response (e.g., a CTL response).

Therefore, the method of the present invention overcomes the preferential induction of a humoral (antibody) response by combining carbohydrate receptor-bearing cells with the antigen:carbohydrate conjugate ex vivo to avoid the circulating cross reactive antibodies upon administration of a therapeutic composition of the present invention to an animal. When introduced into a patient, a cellular immune response, and particularly a CTL and/or T1 (TH1) response, is preferentially induced by the cells presenting an antigenic peptide of the antigen of interest. The method comprises the steps of administering to an animal a carbohydrate receptor-bearing cell that has been contacted with a conjugate comprising antigen and oxidized carbohydrate, in which the carbohydrate receptor-bearing cells are capable of presenting the antigen to a T cell in such a manner that a response is elicited from the T cell. A preferred antigen for use with the present method is mucin. A preferred carbohydrate for use with the present method is mannose.

The following examples are provided for the purposes of illustration and are not intended to limit the scope of the present invention.

Example 1

This example describes that targeting the mannose 1 receptor in vivo gives rise to T cellular immune responses.

A. In Vitro Exposure of Peritoneal Exudate Cells to Mannan-MUC1

Peritoneal exudate cells (PEC) were prepared as follows. Mice were sacrificed, injected intraperitoneally with 10 ml phosphate buffer saline (PBS), gently massaged and peritoneal cells were collected. Adherent PECs were prepared by plating about $2 \times 10^6$/ml PEC in tissue culture plates and incubating 6 at about 37° C. for about 16 to about 24 hours. Non-adherent o PEC cells were dislodged with a pipette and adherent PEC cells were used in the studies described below.

About $4 \times 10^6$ cells PECs from DBA/2 (H-2°) mice, after 6 d adherence for about 16 to about 24 hours, were primed with either 20 µg/ml oxidized-mannan-MUC1 fusion protein (ox-M-FP; described in detail in Apostolopoulos et al., Proc. Natl. Acad. Sci. USA, 92:10128-10132, 1995a and Apostolopoulos et al., J. Immunol., 155:5089-5094, 1995b), reduced-mannan-MUC1 fusion protein (red-M-FP), or non-treated MUC1 fusion protein (FP; containing a peptide of 105 amino acids containing 5 VNTR repeats fused to glutathione-S-transferase, as described in detail in Apostolopoulos et al., Br. J. Cancer, 67:713-720, 1993) or mannan-ox-glutathione-S-transferase (M-GST; described in detail in Apostolopoulos et al., ibid., 1993). Each group of primed cells were transferred by intraperitoneal injection into DBA/2 mice.

The mice were then tested for a cytotoxic T cell (CTL) response by measuring CTL precursor (CTLp) frequencies as follows. CTLp frequencies were determined using a minimum of 32 replicates of at least 6 effector cell doses by culturing the cells in U-bottomed microtiter trays, with about 2 to about $5 \times 10^5$ DBA/2 stimulator spleen cells treated with 5 mitomycin C at a dose of about 25 µg/ml for about 1 to about 1.5 hours, in Dulbeco's modified Eagle's medium containing 10% fetal calf serum, 5 mM synthetic MUC1 peptide (consisting of 2 VNTR repeats; as described in Apostolopoulos et al., ibid., 1995a) and about 10 U/ml recombinant human IL-2. Seven days later, each microculture was assayed for cytotoxicity by replacing 100 µl of culture medium with 100 ml target cell suspension containing about $10^4$ $^{51}$Cr-labeled MUC1$^{30}$P815 tumor target cells (P815 cells transfected with a cDNA encoding human MUC1; obtained as a gift from Dr. B. Acres, Transgene, Strasbourg, France). Cultures with cells having cytotoxic activity were identified by $^{51}$Cr release of about 3 standard deviations above the mean isotope release obtained from about $10^4$ target cells added to responder cells cultured either alone, or with stimulator cells and recombinant IL-2 but without MUC1 synthetic peptide. A linear relationship existed between the dose of responder cells, represented on a linear scale, and the frequency of negative wells on a logarithmic scale; CTLp frequencies were determined as the inverse of responder cell dose required to generate 37% negative wells.

Referring to FIG. 1, the results indicated that the CTLp frequency obtained following a single immunization with the PEC pulsed in vitro with Ox-M-FP was approximately the same (1/7,000) as that obtained after 3 in vivo immunizations of the cell free proteinaceous form of Ox-M-FP. A single injection of PEC pulsed in vitro with red-M-FP or FP generated a CTLp frequency of 1/28,000 and 1/29,600, respectively. Three intraperitoneal injections of either red-M-FP or FP gave CTLp frequencies of 1/89,000 and 1/87,500 respectively. Cells primed with M-GST gave a frequency of 1/800,000. In all cases the response was MUC1 specific because non-transfected P815 target cells were not lysed. Taken together, the results indicate that ox-M-FP, delivered either by multiple injections of the fusion protein or by a single injection of PECs pulsed in vitro with ox-M-FP, stimulates a higher CTL response than red-M-FP or FP alone delivered by either route. The presence of mannose on the red-M-FP provides no selective advantage (compared to non treated FP) when delivered in vivo as a fusion protein. Targeting of red-M-FP or FP to the mannose receptor by in vitro pulsing of PECs with these proteins and then using these cells for immunization, however, was more effective at eliciting CTLp (frequency approx 1/28,000 for both) than the injection of these fusion proteins (1/80,000 for both). Thus, pulsing PECs in vitro with Ox-M-FP (and thereby targeting to the mannose receptor) gives a better CTL response than pulsing PECs in vitro with red-M-FP or FP. In addition, injection of the fusion protein Ox-M-FP, but not red-M-FP or FP, enhances the CTLp frequency. Finally, the pulsing of PECs with red-M-FP or FP in vitro enhances the generation of CTLp compared with the in vivo injection of these proteins.

Figure 2:
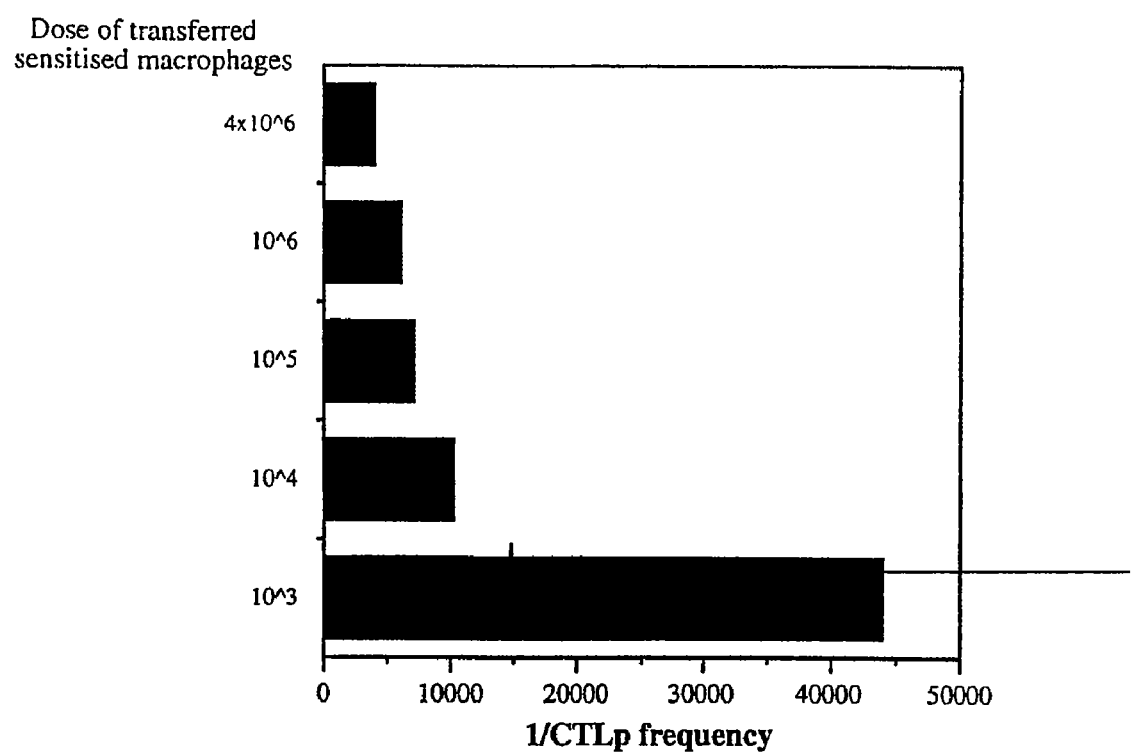
FIG. 2 illustrates the minimum number of antigen presenting mannose receptor-bearing cells needed to induce a T cell response.

Referring to FIG. 2, a dose response of the number of in vitro sensitized PECs injected, indicated that the minimum number of PECs required to enhance the CTLp frequency was $10^4$ cells. $10^4$ cells gave a CTLp frequency (1/10,200), not substantially different than that obtained with 400 times more cells ($4 \times 10^6$ cells; CTLp frequency 1/4,000). Thus, at numbers greater than $10^4$ transferred PECs, the CTLp frequency was not dose-dependent on the number of transferred cells and was similar in the range of $10^4$-$4 \times 10^6$ cells. When $10^3$ cells were transferred, the CTLp frequency fell to 1/44,000.

Figure 3:
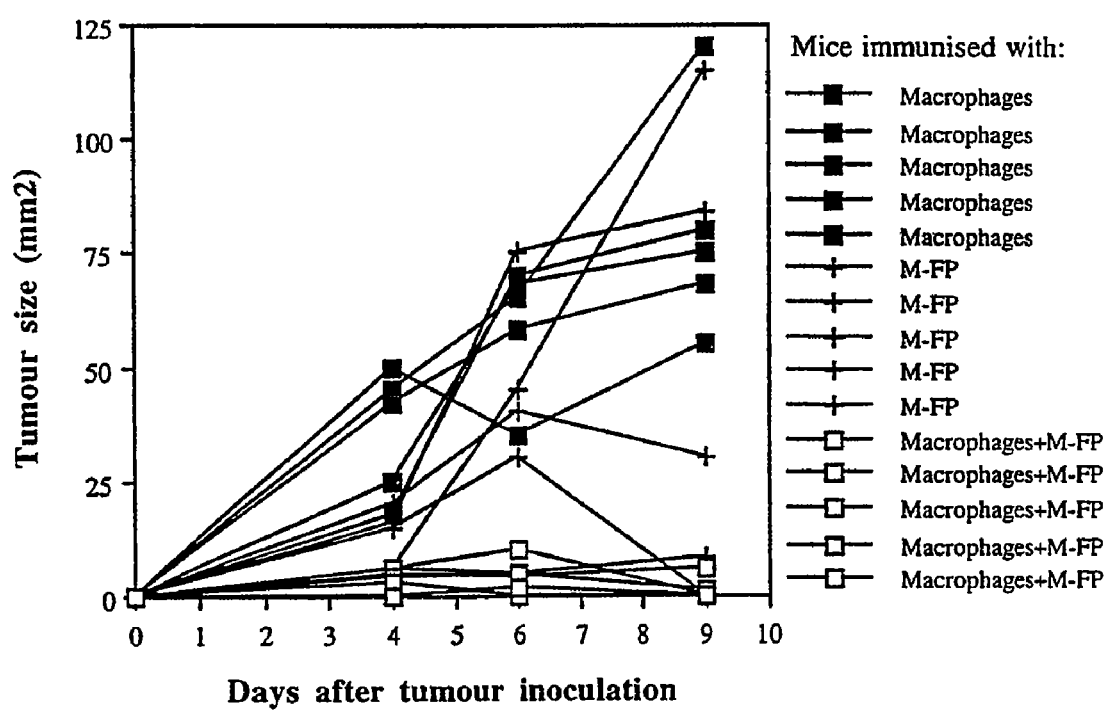
FIG. 3 illustrates tumor growth in mice immunized with peritoneal exudate antigen presenting mannose receptor-bearing cells pulsed with oxidized MUC1, oxidized mannan fusion protein or buffer alone.

B. Mice Immunized with In Vitro Pulsed PECs were Protected from a Tumor Challenge To examine the ability of the sensitized PECs to elicit protective responses against tumor challenge, groups of 5 DBA/2 mice were injected once with either ox-M-FP, or PECs pulsed with ox-M-FP, or with non-pulsed PECs, and then challenged with $5 \times 10^6$ MUC1+P815 cells. Referring to FIG. 3, the results indicated that there was no detectable tumor growth in any of the five mice immunized with PECs primed with oxidized-M-FP. Conversely, three of five mice immunized once with oxidized-M-FP developed tumors and five of five mice immunized once with non-pulsed PECs developed tumors.

Thus, PECs derived from the peritoneal cavity of mice and cultured in vitro with oxidized-M-FP can, after adoptive transfer, efficiently process and present a MUC1 antigen, leading to the generation of high frequency of CTLs, and protection against a subsequent tumor challenge.

C. Binding Studies of Reduced and Oxidized M-FP

Experiments were performed to analyze the binding of the different mannan forms to different types of tissues, cell lines, cells and receptors. Table 1 summarizes the results of such binding studies.

TABLE 1

Binding studies of mannan, oxidized mannan or reduced mannan (FITC labeled)

| Cell | Mannan | Oxidized Mannan | Reduced Mannan |
|---|---|---|---|
| Cell lines | − | − | − |
| 3T3 (fibroblast) | − | − | − |
| P815 (mastocytoma) | − | − | − |
| NS1 (B cell line) | − | − | − |
| Sultan (B cell line) | − | − | − |
| EL-4 (T cell line) | − | − | − |
| RMA (T cell line) | − | − | − |
| E3 (T cell line) | − | − | − |
| CEM (T cell line) | − | − | − |
| MM200 (melanoma) | − | − | − |
| COS (kidney cell line) | − | − | − |
| BHK (kidney cell line) | − | − | − |
| J774 (macrophage) | + | + | + |
| D2SC/1 | ± | − | ± |
| Carbohydrate inhibition studies (+ denotes binding of the FITC-mannan; whereas − denotes inhibition) | | | |
| J774 (macrophage) | + | − | + |
| N-acetylgalactosamine | − | + | − |
| galactose | + | + | + |
| glucose | + | + | + |
| mannan | − | − | − |
| mannose | − | − | − |
| L-fucose | − | − | − |
| D-fucose | + | + | + |
| Tissues | | | |
| Spleen | + | + | ++ |
| Lymph node | + | + | + |
| Thymus | − | − | − |
| Cells | | | |
| Macrophages (F4/80) | + | + | + |
| Dendritic (33D1) | − | − | − |
| Receptors | | | |
| Mannose (COS) | ++ | + | ++ |
| Mannose (Western) | ++ | ++ | ++ |
| Scavenger (ScR) using CHO transfectant cell lines, ScR GKO mice and inhibitors for ScR | ± | ± | ± |
| Sialoadhesin | − | − | − |
| CR3 | − | − | − |

− = negative, ± = weak, + = strong, ++ = very strong

1. Cell Lines

Either reduced or oxidized mannan conjugated with fluorescein isothiocyanate (FITC available from Sigma, St. Louis, Mo.; described in detail in Apostolopoulos et al., ibid., 1995a) were mixed with various types of cells using methods generally described in Apostolopoulos et al., ibid., 1995a. Neither FITC-conjugated reduced, or oxidized, mannan bound to the following cell lines: 3T3 (fibroblast) cells, P815 (mastocytoma) cells, NS1 and Sultan (B cell lines) cells, EL-4 cells, RMA cells, E3 cells and CEM (T cell lines) cells, MM200 (melanoma) cells, COS cells and BHK (kidney cell lines) cells. Both FITC-conjugated reduced-, and FITC-conjugated oxidized-, mannan bound to J774 (macrophage cell line, obtained as a gift from Dr. P. Ricciardi-Castagnoli, Milan, Italy) cells. Binding to the dendritic cell line, D2SC/1, was negative with oxidized-mannan-FITC and very weak with reduced-mannan-FITC (Table 1).

Inhibition studies were performed using carbohydrates to inhibit the binding of oxidized or reduced mannose conjugated with FITC; to J774 cells. Binding of oxidized-mannan-FITC to J774 cells was inhibited by mannan, D-mannose, L-fucose and N-acetylglucosamine whereas binding of reduced-mannan-FITC was inhibited by mannan, D-mannose, L-fucose and N-acetylgalactosamine; other sugars (glucose, D-fucose and galactose) did not inhibit (Table 1). The ability of these sugars to inhibit the binding of the FITC conjugated mannan forms is indicative of their binding to the mannose receptor.

2. Tissues

Reduced and oxidized mannan-FITC were injected into mice intraperitoneally and after 1 hour organs were fixed in 4% paraformaldehyde and analyzed by confocal microscopy using standard methods. Both the oxidized and reduced material was found in the liver where the staining was around the sinusoids which is rich in Kuppfer cells; in the spleen where the staining was around the white pulp and in the red pulp where the staining was with the marginal zone macrophages. The results are summarized in Table 1.

3. Receptors

COS cells transfected with a nucleic acid molecule encoding the mannose receptor were mixed with either red-M-FP or ox-M-FP under conditions that allowed for binding of the M-FP to mannose receptor. M-FP binding to mannose receptor was confirmed by resolving M-FP complexed to receptor by SDS-PAGE gel, blotting the protein separated on the gel and resolving bands by Western blot using an antibody that binds specifically to the mannose receptor. The results indicated that both red-M-FP and ox-M-FP also bound to the mannose receptor.

4. Characterization of PEC

The cell surface markers used to define macrophages and dendritic cells were F4/80, 33D1 and NLDC-145. Macrophages were classified as F4/80$^+$33D1$^-$ and dendritic cells were classified as F4/80$^+$33D1$^-$. Adherent PECs were analyzed by flow cytometry as follows. Adherent PECs were stained using standard techniques with either F4/80 antibody (a rat anti-mouse monoclonal antibody that detects macrophages but not dendritic cells; described in Austyn et al., Eur. J. Immunol., 11:805-812, 1981 and Nussenzweig et al., J. Exp. Med., 4:168-179, 1981); 33D1 antibody (a rat anti-mouse monoclonal antibody that reacts with mouse dendritic cells but not 15 macrophages; described in Steinman, et al., J. Exp. Med., 157:613-627, 1983); and NLDC-145 antibody (a rat anti-mouse monoclonal antibody that detects the DEC-205 molecule on dendritic cells, which is absent from macrophages; described in Swiggard, et al., Cell. Immunol., 165:302-11, 1995 and provided as a gift by Dr. Derek Hart, Christchurch Hospital, Christchurch, New Zealand). The stained cells were resolved by flow cytometry using standard methods. For serological studies; about 100 µl of each antibody was added to about 2×10$^5$ PEC cells and incubated for about 1 hour at about 4° C. The cells were washed three times with about 0.5 ml PBS. About 100 µl of a 1:50 dilution of FITC-conjugated sheep (Fab') anti-mouse immunoglobulin (available from Silenus, Australia) was added to each sample and incubated for about 45 minutes at about 4° C. The cells were washed again and then analyzed by flow cytometry, using a FACScan flow cytometer.

The results are summarized in Table 2 and indicate that about 75% of the adherent PECs were F4/80$^+$; about 30% were NLDC-145$^+$ and about 33% were 33D1$^+$. About 5% of the adherent PECs were double positive (F4/80$^+$ 33D1$^+$).

TABLE 2

Phenotype of cells by flow cytometry

| PEC Cells Monoclonal antibodies to: | % positive |
|---|---|
| F4/80 | 75 |
| NLDC-145 | 30 |
| 33D1 | 33 |
| PBS | 7 |

| Cells | % positive staining antibodies to: | | | |
|---|---|---|---|---|
| | F4/80 | 33D1 | NLDC-145 | PBS |
| F4/80$^+$/33D1$^-$ | 80 | 17 | 12 | 14 |
| F4/80$^-$/33D1$^+$ | 3 | 85 | 3 | 3 |

| | % positive staining with FITC conjugated mannan forms | | | |
|---|---|---|---|---|
| | Mannan | OxMannan | RedMannan | PBS |
| F4/80$^+$/33D1$^-$ | 46 | 70 | 52 | 7 |
| F4/80$^-$/33D1$^+$ | 3 | 3 | 5 | 5 |

A population of adherent PECs were then separated using Dynabeads™ into two populations. One population (macrophage enriched) was comprised of about 80% F4/80$^+$, about 13% 33D1$^+$, about 14% F4/80$^-$ 33D1$^-$. The second population (dendritic cell enriched) was about 3% F4/80$^+$, about 85% 33D1$^+$ and about 3% F4/80$^-$ 33D1$^-$ (see Table 2). The method used to derive these two populations is as follows: Dynabeads (M-450) that were coated with antibody to sheep anti-rat IgG, were mixed with 30 either of the two rat monoclonal antibodies, F4/80 or 33D1, for 3 hours at 4° C. These treated Dynabeads were then added separately to 10$^7$ PECs and mixed for 30 minutes at 4° C. The cells which had bound to the antibody coated Dynabeads were removed with a magnet and the cells which had not bound Dynabeads were collected for further study. A sample of these cells which had not bound Dynabeads was tested by flow cytometry for the ability to bind the F4/80 or the 33D1 antibody. The rest of the cells which had not bound Dynabeads were then incubated with ox-M-FP for 16 to 24 hours and adoptively transferred into the peritoneum of syngeneic mice using the method described above in section A (see next example).

The macrophage (33D1$^-$) and dendritic cell (F4/80$^-$) enriched populations described immediately above were further characterized for expression of the mannose receptor by flow cytometry using mannan-FITC, oxidized mannan-FITC or reduced mannan-FITC. About 100 µl of each FITC conjugate was added to about 2×10$^5$ macrophage or dendritic cell enriched populations and incubated for about 1 hour at about 4° C. The cells were washed three times with about 0.5 ml PBS. The cells were analyzed by flow cytometry, using a FACScan flow cytometer. Referring to Table 2, about 46% of the cells in the F4/80$^+$ 33D1$^-$ population were stained with mannan-FITC and 58% of the cells in this population bound both mannan-FITC and F4/80 antibody. The F4/80$^-$ 33D1$^+$ population did not bind mannan-FITC (5% or less, which was the number of positive cells in the sample which received PBS). About 52% of the F4/80$^+$ population stained with reduced-M-FITC (65% of the cells in this population bound both reduced-mannan-FITC and F4/80 antibody). Again the 33D1$^+$ cell population did not bind reduced-mannan-FITC. About 70% of F4/80$^+$ population stained with oxidized-M-FITC and 58% of the cells in this population bound both oxidized-mannan-FITC and F4/80 antibody. Again the 33D1$^+$ cell population did not bind oxidized-mannan-FITC. Thus, both forms of mannan (reduced and oxidized) bind to macrophages but not to dendritic cells, with the oxidized material binding best.

5. Determination of the Preferential Role of Macrophages and Dendritic Cells in the PEC Population PEC were separated into two populations containing either 80% F4/80$^+$ 33D1$^-$ macrophage enriched cells and 85% F4/80$^-$ 33D1$^+$ dendritic cells using either F4/80 or 33D1 antibodies and Dynabeads as described above in section D. The separated macrophage and dendritic cell populations were cultured separately in vitro with about 20 µg of M-FP for about 16 to about 24 hours. An unfractionated PEC population was cultured similarly. The cell populations were then injected intraperitoneally into separate mice and the MUC1 specific CTLp frequencies were determined using the methods generally described above in section A.

TABLE 3

CTLp in mice immunized with adoptively transferred cells

| Cells | Number of cells transferred | CTLp frequency* |
|---|---|---|
| PEC | 1 × 10$^6$ | 1/11,000 |
| F4/80$^+$(Mac) | 6 × 10$^5$ | 1/15,000 |
| 33D1$^+$(DC) | 2 × 10$^5$ | 1/64,000 |
| F4/80$^+$(Mac) | 2 × 10$^5$ | 1/13,000 |
| 33D1$^+$(DC) | 2 × 10$^5$ | 1/65,000 |
| J774 (Mac) | 1 × 10$^6$ | 1/33,000 |
| D2SC/1 (CD) | 1 × 10$^6$ | 1/130,000 |

*average of 2 individual mice

Referring to Table 3, the results indicated that injection of 10$^6$ in vitro pulsed PEC produced a CTLp frequency of 1/11,000. Similarly, 6×10$^5$ pulsed macrophages produced a CTLp frequency of 1/15,000 whereas 2×10$^5$ dendritic cells produced a CTLp frequency of 1/64,000. Thus, the mannose receptor positive, F4/80$^+$ macrophages were primarily responsible for the increase in CTLp frequency. The dendritic cells, which are mannose receptor negative, were less effective in enhancing the CTLp frequency. In the above experiment the number of injected macrophages (6×10$^5$) was different from the number of injected dendritic cells (2×10$^5$). A comparison was subsequently made using the same dose (2×10$^5$) of each of the cell types. Macrophage and dendritic cell populations were prepared as described immediately above and injected into mice. About 2×10$^5$ macrophages and about 2×10$^5$ dendritic cells were injected into separate mice and the MUC1 specific CTLp frequency determined. Injection of the macrophages produced a CTLp frequency of 1/13,000 whereas injection of the dendritic cells produced a CTLp frequency of 1/65,000 (see Table 3). Thus, the macrophages are the major effector cells in generating high CTLp frequency when mice receive cells pulsed in vitro with ox-M-FP.

The role of the dendritic cells in MUC1 antigen presentation was also determined by immunizing BALB/c mice once with about 10$^6$ J774 cells pulsed in vitro with ox-M-FP for 16 to 24 hours. The J774 cells produced a CTLp frequency of 1/33,000 (see Table 3). BALB/c mice were also immunized once with D2SC/1 cells (a dendritic cell line) pulsed with ox-M-FP for 16 to 24 hours. Injection of D2SC/1 cells produced a CTLp frequency of 1/130,000 (see Table 3). These results demonstrate that macrophages pulsed with ox-M-FP are more effective than dendritic cells pulsed with ox-M-FP at increasing the CTLp frequency.

Figure 4:
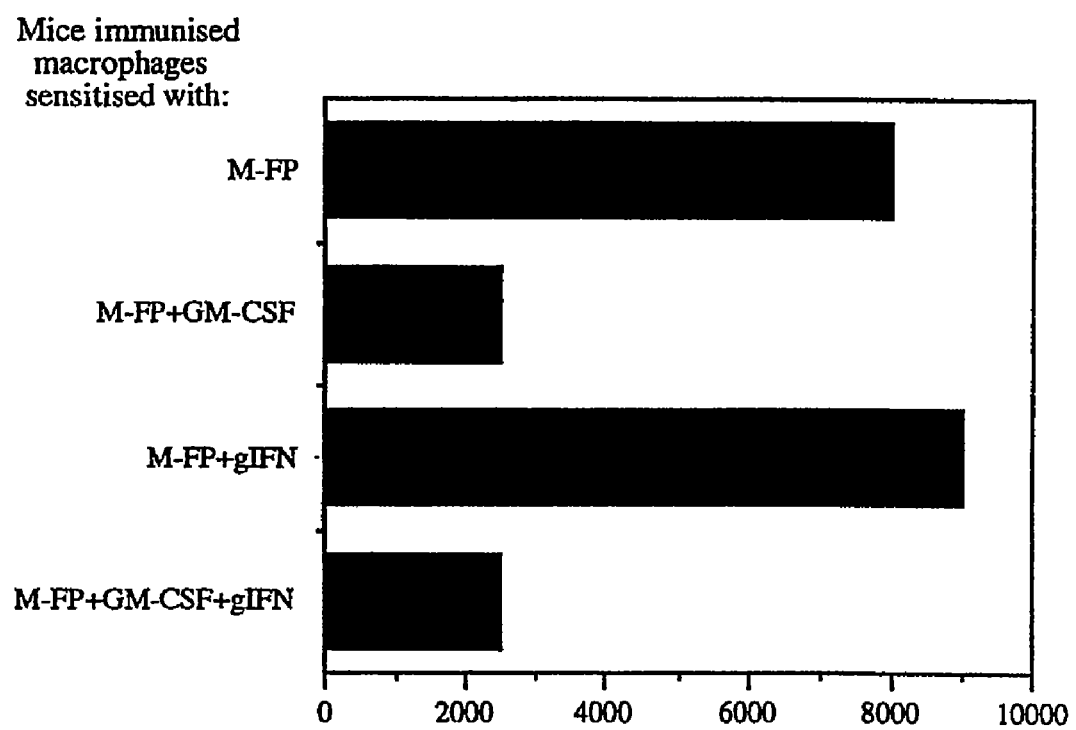
FIG. 4 illustrates CTLp frequencies using peritoneal exudate cells, containing antigen presenting mannose receptor bearing cells, treated with GM-CSF or interferon gamma and pulsed with oxidized mannan fusion protein.

6. Effect of GM-CSF on the Immune Responses Generated with PEC Pulsed with ox-M-FP PECs were isolated from mice, adhered to plastic, pulsed with oxidized-M-FP and incubated with either GM-CSF (about 10 ng/ml) or with gamma interferon for about 3 hours, in vitro. Some cells were incubated with ox-M-FP for about 3 hours in the absence of cytokine. Referring to FIG. 4, the cells were then transferred to separate naive mice. Transfer of the GMCSF treated cells produced a CTLp frequency of 1/2,500. Transfer of the untreated cells produced a CTLp frequency of 1/7,000. Conversely, transfer of cells treated with gamma interferon produced a CTLp of 1/9,000.

Figure 5:
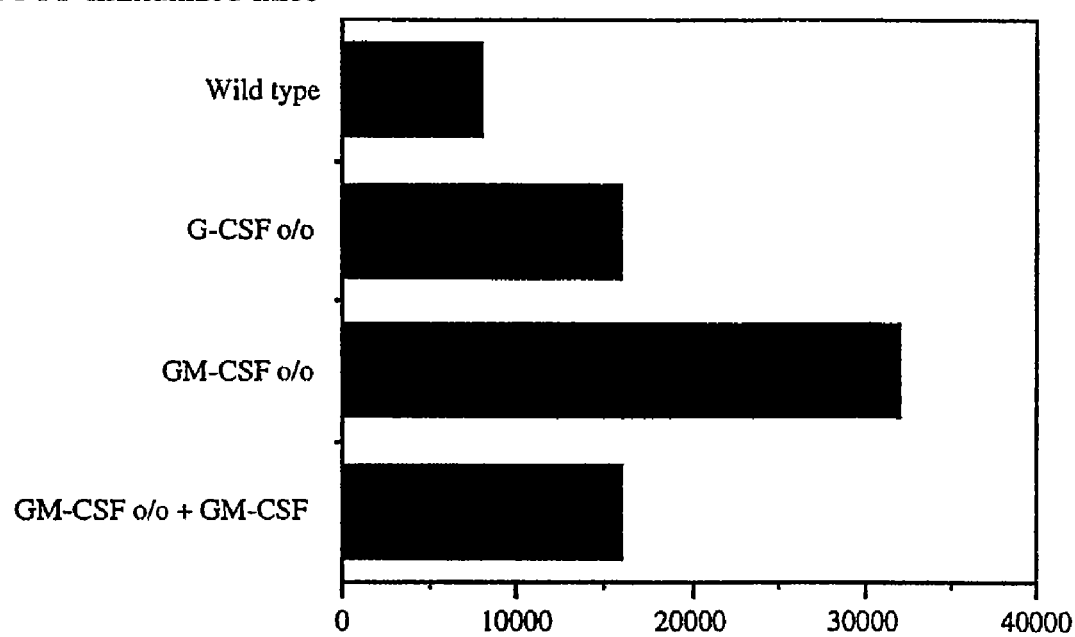
FIG. 5 illustrates CTLp frequencies of GM-CSF or G-CSF knockout mice immunized with oxidized mannan fusion protein.

In another study, PECs were isolated from mice, adhered to plastic and pulsed with ox-M-FP. The pulsed cells were then injected into either GM-CSF o/o mice (mice lacking GM-CSF produced by homologous recombination; obtained from Dr. Ashley Dunn), G-CSF o/o mice (mice lacking G-CSF produced by homologous recombination; obtained from Dr. Ashley Dunn) or wild type mice. This process was repeated for a total of three injections for each mouse. Referring to FIG. 5, the results indicated that transfer of PECs isolated from the wild 25 type mice produced a CTLp frequencies of 1/8,000 in wild type mice, 1/16,000 in G-CSF o/o mice and 1/32,000 in GM-CSF o/o mice. The GM-CSF o/o mice were further immunized with M-FP and were also given GM-CSF. The CTLp frequency present in these mice increased to 1/16,000. Thus, the CTLp response to PECs pulsed in vitro with ox-M-FP is partially GM-CSF dependent and can be augmented by GM-CSF.

Figure 6:
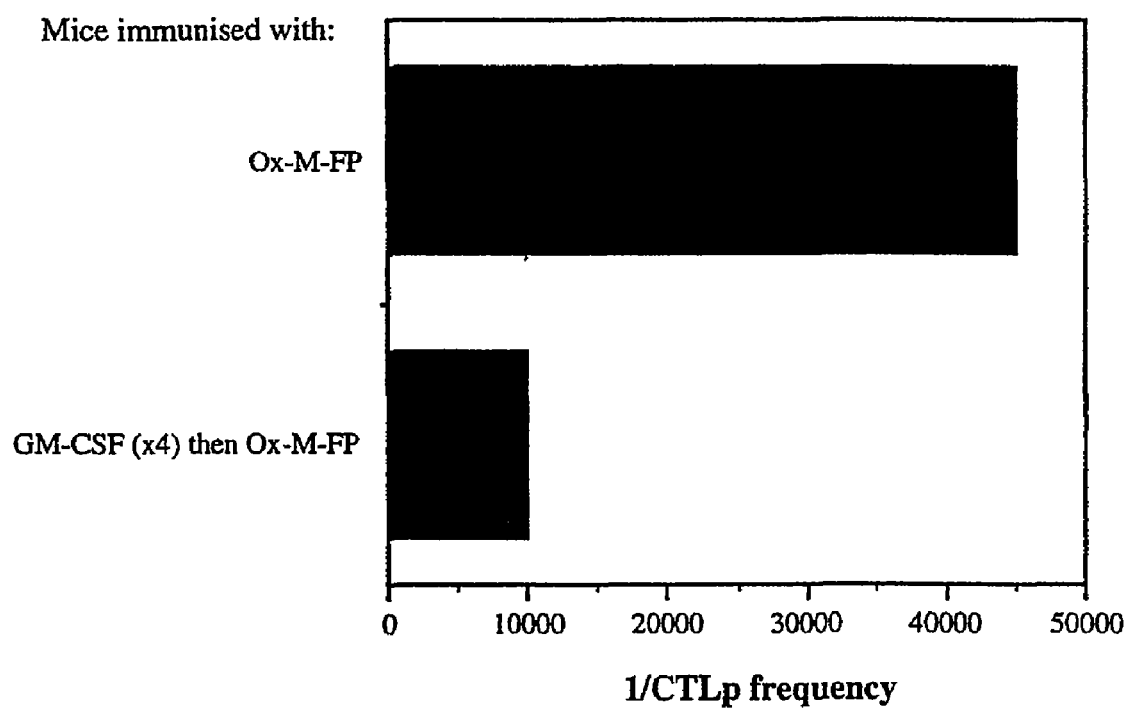
FIG. 6 illustrates CTLp frequencies in mice injected with GM-CSF prior to injection with oxidized mannan fusion protein.

In another study, wild type mice were injected intraperitoneally with 1 µg of recombinant GM-CSF per day for either 2, 3, 4, 5, or 6 days. PECs were isolated from these 10 mice, counted and stained using F4/80 or 33D1 antibodies and standard methods. Stained cells were then detected by flow cytometry using standard methods. About 10$^6$ resident PEC cells/mouse was isolated after one day (1 injection). About 9.6×10$^6$ macrophages (F4/80$^+$ cells) were obtained after 2 days (2 injections), about 1.2×10$^7$ macrophages after 3 days (3 injections), and about 2×10$^7$ macrophages after 4 to 6 days (4 to 6 injections). Four days of GM-CSF injections were optimal in isolating the most number of macrophages. A group of mice was then injected with 1 µg of recombinant GM-CSF per day for 4 days. On the fifth day, a single injection of ox-MFP was then administered to these mice as well as to a group of mice that had not been treated with GM-CSF. Referring to FIG. 6, mice that were treated with GM-CSF and then received one injection of ox-M-FP had a CTLp frequency of 1/9,900. Mice that did not receive GM-CSF, but were given one injection of ox-M-FP had a CTLp frequency of 1/45,000. Thus the CTLp response to injection of the Ox-M-FP protein can be enhanced by the administration of GM-CSF.

7. Transfer of Semi-Allogeneic Macrophages in Mice

Figure 7:
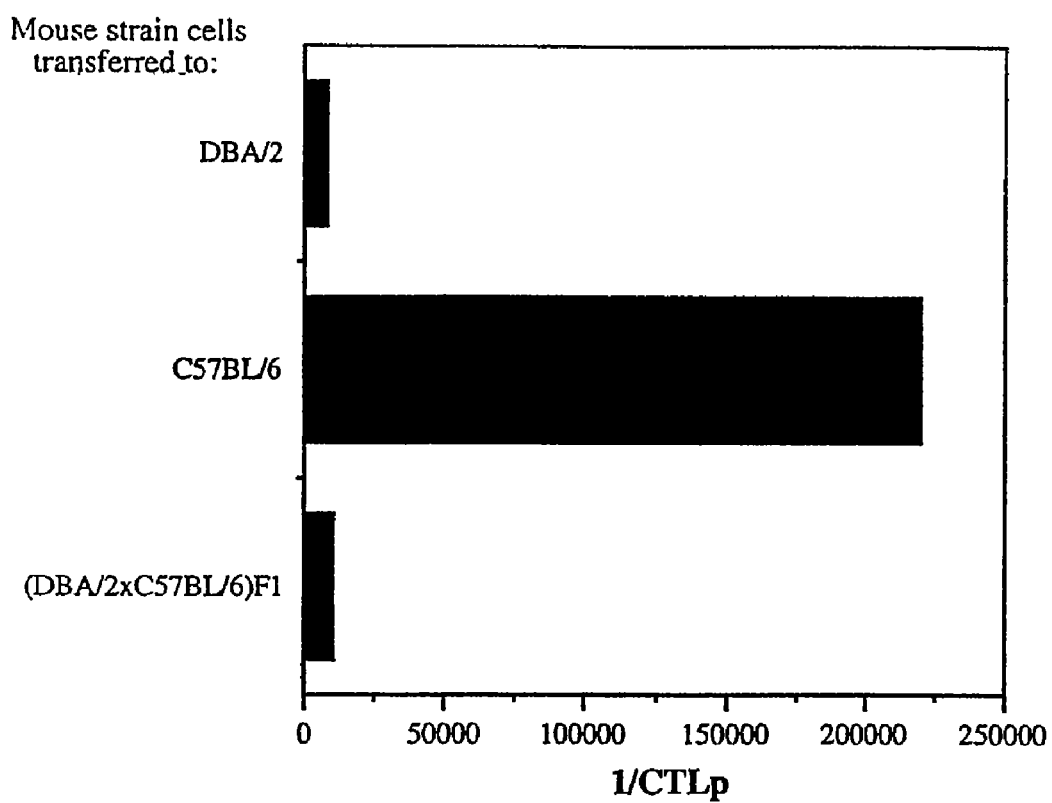
FIG. 7 illustrates CTLp frequencies in semi-allogeneic and allogenic recipients of macrophages pulsed with oxidized mannan fusion protein.

Macrophages isolated from DBA/2 mice were either pulsed, or not pulsed, with ox-M-FP as described above. The two cell populations were then injected separately into either DBA/2, C57BL/6 or (DBA/2×C57BL/6)F1 mice. Referring to FIG. 7, injection of the pulsed macrophages into DBA/2 mice produced a CTLp frequency of 1/8,000; injection of the pulsed macrophages into C57BL/6 mice produced a CTLp frequency of 1/220,000; and injection of the pulsed macrophages into (DBA/2×C57BL/6)F1 mice produced a CTLp frequency of 1/10,000. Mice injected with non pulsed macrophages had a CTLp frequency of <1/10$^6$. The same methods described immediately above were repeated, except that the PECs were isolated from (DBA/2×C57BL/6)F1 mice and, following pulsing with ox-M-FP, were injected into either C57BL/6 or DBA/2 mice. Transfer of ox-MFP pulsed PECs from (DBA/2×C57BL/6)F1 mice into either C57BL/6 or DBA/2 mice produced a high CTLp frequency. Thus the immune response can be transferred semi-allogeneically (i.e. where one haplotype is shared). Taken together, the results described in sections A through G indicated that culturing macrophage cells with ox-M-FP, and adoptively transferring the cells to syngeneic mice, induces a specific CTL response to MUC1. In addition, one immunization of macrophages pulsed with oxidized-M-FP led to protection from MUC1+ tumors. The single immunization with macrophages pulsed in vitro with ox-M-FP provides an increase in CTLp equivalent to that conferred by three immunizations with the ox-M-FP fusion protein. Thus, targeting the mannose 1 receptor by in vitro pulsing with ox-M-FP, gives rise to T cellular immune responses.

Example 2

This example describes the comparison between reducing agents sodium borohydride and sodium cyanoborohydride.

Ox-M-FP was prepared as described above in Example 1. Three different samples were prepared as follows. A portion of ox-M-FP was combined with 0.5 mg/milliliter (ml) of sodium borohydride to reduce Schiffs bases and aldehydes. Another portion of ox-M-FP was combined with 0.5 mg/ml of sodium cyanoborohydride to reduce predominantly Schiff bases only. A third portion remained untreated. 5 µg of each of the three samples were injected into separate mice. Cytotoxic T cell frequencies (CTLp) were determined using the methods generally described above in Example 1.

The results indicated that the CTLp frequency induced by ox-M-FP treated with sodium cyanoborohydride was 1/10, 300. The CTLp frequency induced by ox-M-FP treated with sodium borohydride was 1/79,500. The CTLp frequency induced by the untreated ox-M-FP was 1/14,575. Taken together, the results indicated that aldehyde groups on ox-M-FP are important for CTL induction.

Example 3

This example describes the effect of culturing peripheral blood mononuclear cells with GM-CSF, IL-3 and vitamin D.

Peripheral blood mononuclear cells (PBMC) were isolated from a normal human donor using standard methods. The freshly isolated PBMC were cultured in wells of a standard 6-well tissue culture plate in serum-free AIM-V medium at a density of 10×10$^6$ cells per 2 ml of medium per well, for 2 hours. Following the incubation step, non-adherent cells were removed from the wells. About 2 ml of fresh serum-free AIM-V medium containing 1 nanogram per ml (ng/ml) GM-CSF, 10 ng/ml of IL-3, 10 ng/ml IL-4, 50 ng/ml TNF alpha and 50 nM vitamin D was added to each well. The cells were incubated for 2, 4 and 7 days.

At each pre-determined time point, cells were collected and analyzed for the expression of mannose receptor as well as cell surface marker that identify monocytes, macrophages and dendritic cells. Expression was determined by FACS analysis using methods generally described above in Example 1. The following reagents were used in the FACS analysis: fluorescein-conjugated (FITC) oxidized mannan (ox-M-FITC; described in Example 1); phycoerythrin (PE) conjugated CD11b, PE conjugated CD11c, PE conjugated CD14, FITC conjugated CD68, FITC conjugated CD80, PE conjugated CD86 and PE conjugated CD54. The results of the FACS analysis are described below in Table 4.

TABLE 4

Percent of monocyte, macrophage and dendritic cells after activation with cytokine*

| Antibody | Day 0 | Day 2 | Day 4 | Day 7 |
|---|---|---|---|---|
| CD54-PE | 40 | 99 | 99 | 99 |
| CD11b-PE | 28 | 97 | 87 | 93 |
| CD11c-PE | 22 | 98 | 93 | 96 |
| CD14-PE | 20 | 92 | 50 | 70 |
| CD68-FITC | 14 | 59 | 27 | 66 |
| CD80-FITC | 17 | 61 | 33 | 44 |
| CD86-PE | 21 | 98 | 92 | 89 |
| Ox-M-FITC | 41 | 69 | 44 | 25 |

*The cells were gated on the large non-lymphocytic population

The cells were gated on the large non-lymphocytic population The highest number of mannose receptor positive cells were generated after 2 days of culture Day 4 of the incubation. This correlates well with an increase in CD54, CD80 and CD86 bearing cells which represent cellular activation markers. Further more were either monocytes or macrophages, but not dendritic cells.

Example 4

This example describes the binding of antibodies to MUC1 and Galα(1,3)Gal antibodies are cross-reactive with Galα(1, 3)Gal and MUC1, respectively.

Several mice were analyzed for the presence of antibodies that bind specifically to Galα(1,3)Gal or MUC1. The sera were obtained from either normal mice, mice in which the Gal gene had been deleted by homologous recombination (gal o/o mice), and mice immunized intraperitoneally, three times with about 5 µg of MUC1 peptide. The presence of antibodies that bind to MUC1 in these sera was determined by their ability to bind to cell lines which either did (BT-20 cells or RMA-MUC1 cells) or did not (ME272 or RMA cells) express MUC1. The binding of antibodies to these cells was determined by FACS analysis using methods generally described in Example 1.

Figure 8:
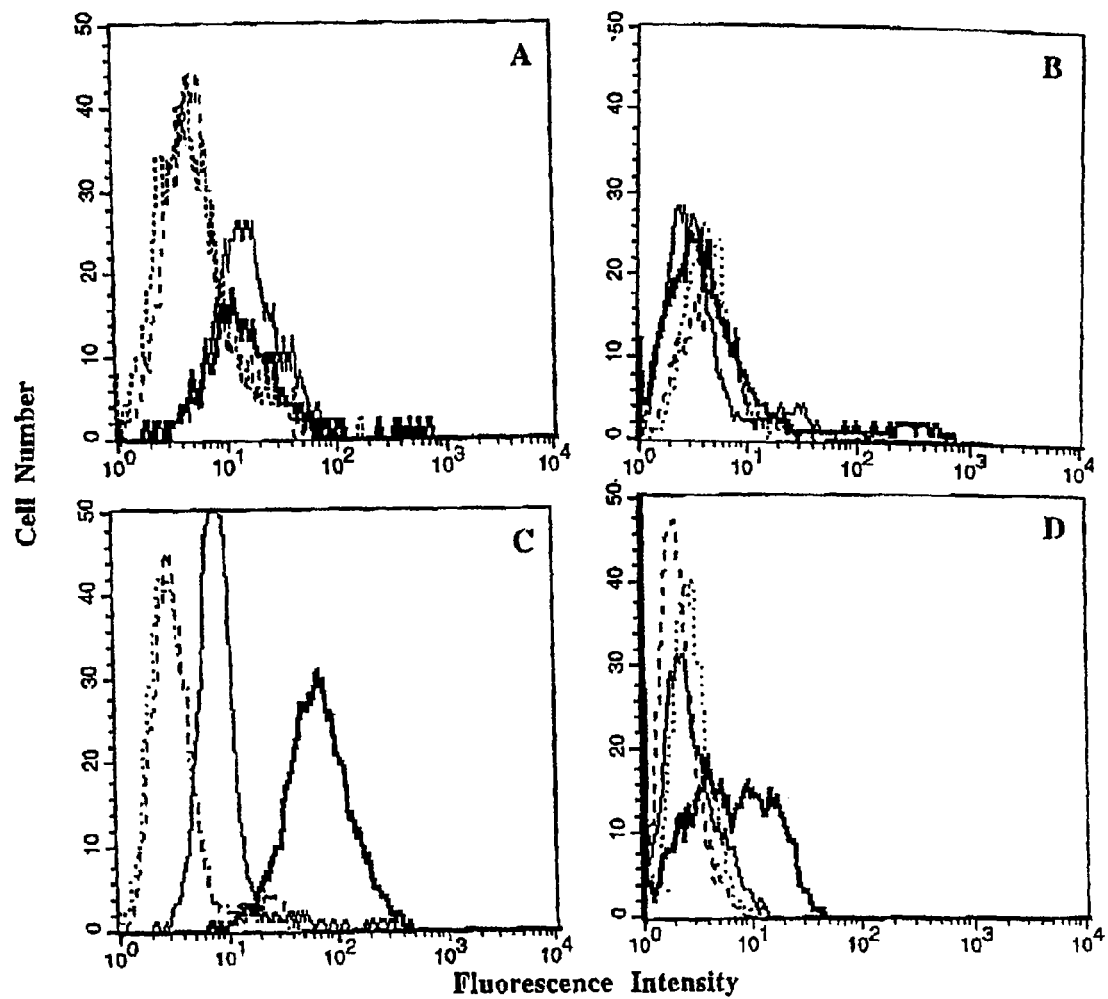
FIG. 8 illustrates FACS analysis of the cross reaction between MUC1 and gal on Gala(1,3)Gal– cell lines and Gala (1,3)Gal+ cell lines.

Referring to FIG. 8, serum from the normal mice did not bind to any of the cell lines. The antiserum raised against MUC1 contained antibodies that bound to BT-20 cells (panel A of FIG. 8) and RMA-MUC1 cells (panel C of FIG. 8), but did not bind to ME272 (panel B of FIG. 8) or RMA cells (panel D of FIG. 8).

The BT-20 cells and ME272 cells do not express Galα(1, 3)Gal, whereas the RMA-MUC1 and RMA cells express Galα(1,3)Gal. Serum from the gal o/o mice contain natural antibodies to galactose as demonstrated by the reactivity with BT-20 cells (MUC⁻gal⁺ cells; panel A of FIG. 8) and RMA-MUC1 cells (MUC⁺gal⁺) cells (panel C of FIG. 8), weak on RMA cells (MUC⁻gal⁺; panel D of FIG. 8) and ME272 cells (MUC⁻gal⁻) were negative. The serum from the gal o/o mice contained antibodies that bound stronger to the RMA-MUC1 cells, which differ from the RMA cells only by the expression of MUC1.

Taken together, the results indicated that expression of MUC1 by RMA cells and expression of MUC1 on BT-20 cells confers reactivity with the anti-gal antibodies present in the gal o/o mice. Thus, naturally-occurring antibodies in gal o/o mice reacted with MUC1 and antibodies raised against MUC1 reacted with Galα(1,3)Gal.

Example 5

This example describes that animals which express Galα (1,3)Gal do not have naturally-occurring antibodies to Galα (1,3)Gal and do not produce antibodies that bind to MUC1 when immunized with oxidized mannan-MUC1. Multiple immunizations of animals with about 5 µg ox-M-FP (described in Example 1) were performed at weekly intervals and were given at the following sites: intraperitoneally in mice; intramuscularly in rabbits and chickens; and into humans and monkeys. Sera obtained from the immunized animals were examined for the presence of antibodies to MUC1 by enzyme-linked immunoassay (ELISA) using the following method. A standard microtiter plate was coated with a 10 µg/ml solution of MUC1 peptide (described above in Example 1) in phosphate buffered saline (PBS), for about 16 hours at 4° C. The unbound peptide was removed from the plate. The plate was washed using standard methods. The plate was then coated with a 2% w/v solution of bovine serum albumin (BSA) for about 2 hours at about 4° C. The was removed from the plate and the plate washed using standard methods. About 50 µl of various dilutions of mouse, rabbit, chicken, human and monkey sera were added to separate wells on the coated plate and incubated for about 2 hours at room temperature. The plate was then washed to remove unbound antibodies. The presence of antibodies bound to the plate from each species of animal was detected using secondary antibodies including sheep anti-mouse antibody to detect mice antibodies; anti-rabbit antibody to detect rabbit antibodies; anti-chicken antibody to detect chicken antibodies; anti-human antibody to detect human antibodies; and anti-monkey antibody to detect monkey antibodies. These antibodies were added to the plate and the plate was incubated for about 1 hour at room temperature. The presence of secondary antibody bound to the plate was detected using about 50 µl of 0.03% 2,2'-azino-di(3)-ethylbenzothiazoline sulfonate (available from Amersham, U.K.), 0.02% hydrogen peroxide in a about 0.1 M citrate buffer, at about pH 4. The reaction was developed for about 10 to about 15 minutes at room temperature and then the absorbance read at 405 nm using an ELISA reader.

Figure 9:
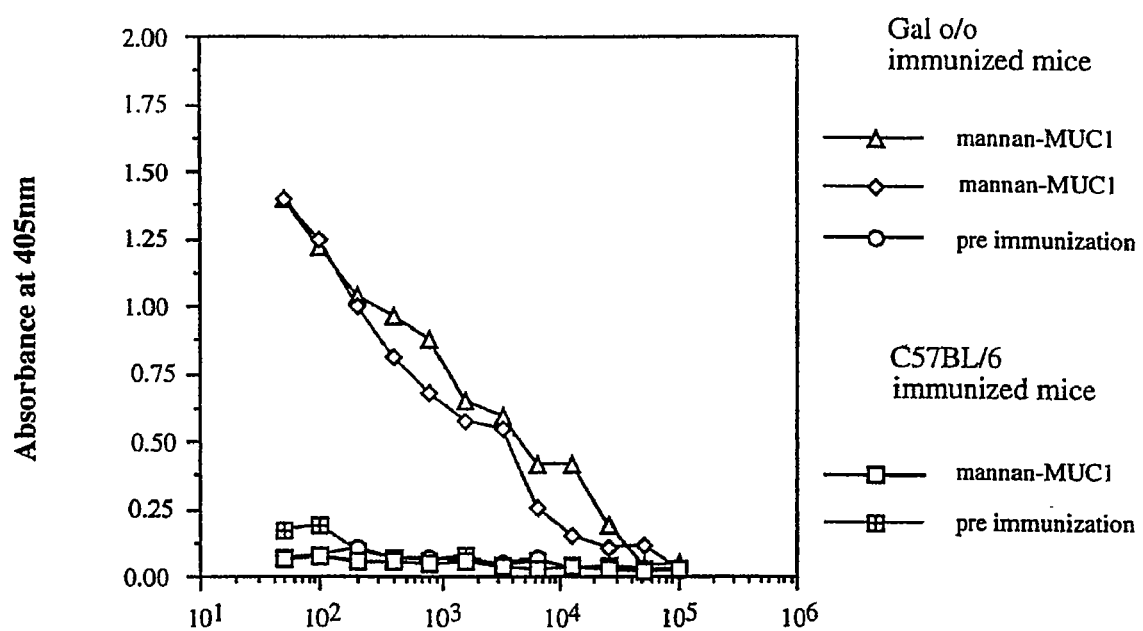
FIG. 9 illustrates the detection of anti-MUC1 peptide antibodies in serum isolated from Gal o/o mice and C57BL/6 mice immunized with oxidized mannan fusion protein.

Referring FIG. 9, immunization of normal C57BL/6 mice with ox-M-FP did not elicit any detectable production of antibodies that bound to MUC1 when immobilized on the microtiter plate. Conversely, immunization of gal o/o mice with ox-M-FP resulted in the production of high titers, about $10^{-4}$ dilution, of antibodies that bound to MUC1. The naturally-occurring antibodies to gal present in the gal o/o mice react with intact MUC1 or MUC1 fusion protein in solution, but do not react with the synthetic peptide of MUC1 immobilized on the microtiter plate. This was indicated that the lack of reactivity of the pre-immune sera from gal o/o mice with immobilized MUC1 peptide (FIG. 9). In addition, several other animals which are negative for Galα(1,3)Gal demonstrated high titers for antibodies that bound to ox-M-FP (see Table 5). Rabbits, which are negative for Galα(1,3)Gal, did not produce antibodies that bound to MUC1. Thus, the animals that were positive for Galα(1,3)Gal (i.e., mice and rabbits), and did not have pre-existing antibodies that bound to galactose, did not produce anti-MUC1 antibodies following immunization with ox-M-FP. In contrast, animals that were negative for galactose (i.e., humans, monkeys, chickens and gal o/o mice), produced anti-MUC1 antibodies in response to immunization with ox-M-FP.

TABLE 5

Immune responses generated in different species immunized with mannan-MUC1

| Species | | Immune Responses | | |
|---|---|---|---|---|
| | | Antibody[a] | CTL[b] | CTLp[c] |
| a) Gal status of species | | | | |
| Galα(1,3)Gal+/ antiGal Ab− | mice (normal) | − | + | ++ |
| | mice (MUC1 Tg[d]) | − | + | + |
| | rabbits | − | NT[e] | NT |
| Galα(1,3)Gal−/ anti-Gal Ab+ | humans | ++ | ±[f] | NT |
| | monkeys | ++ | − | +[g] |

TABLE 5-continued

Immune responses generated in different species immunized with mannan-MUC1

| Species | Immune Responses | | |
|---|---|---|---|
| | Antibody[a] | CTL[b] | CTLp[c] |
| chickens | ++ | − | NT |
| mice (gal o/o) | ++ | NT | ± |
| b) immune responses in normal mice immunized with mannan-MUC1 in the presence of serum (NMS or gal o/o serum) | | | |
| NMS[h] | − | NT | ++ |
| Gal o/o serum | ++ | NT | ± |
| c) immune responses in mice immunized with macrophages pulsed with mannan-MUC1 in the absence of presence of NMS or gal o/o serum | | | |
| Normal mice | − | NT | ++ |
| +NMS | − | NT | ++ |
| +Gal o/o serum | ++ | NT | ± |
| Gal o/o mice | − | NT | ++ |

[a]− = titre <1/50, ++ = titre >1:500
[b]− = negative, ± = weak, + = strong
[c]± = <1/50,000, + = between 1/15,000 and 1/50,000, ++ = >1/15,000
[d]Tg = transgenic;
[e]NT = not tested;
[f]2/10 patients generated a weak CTL response[9];
[g]1/4 monkeys generated a weak CTLp response (Submitted);
[h]NMS, normal mouse serum Example 6

This example describes that animals that are positive for Galα(1,3)Gal generate CTLp, rather than antibody, in response to immunization with mannan-MUC1.

Figure 11:
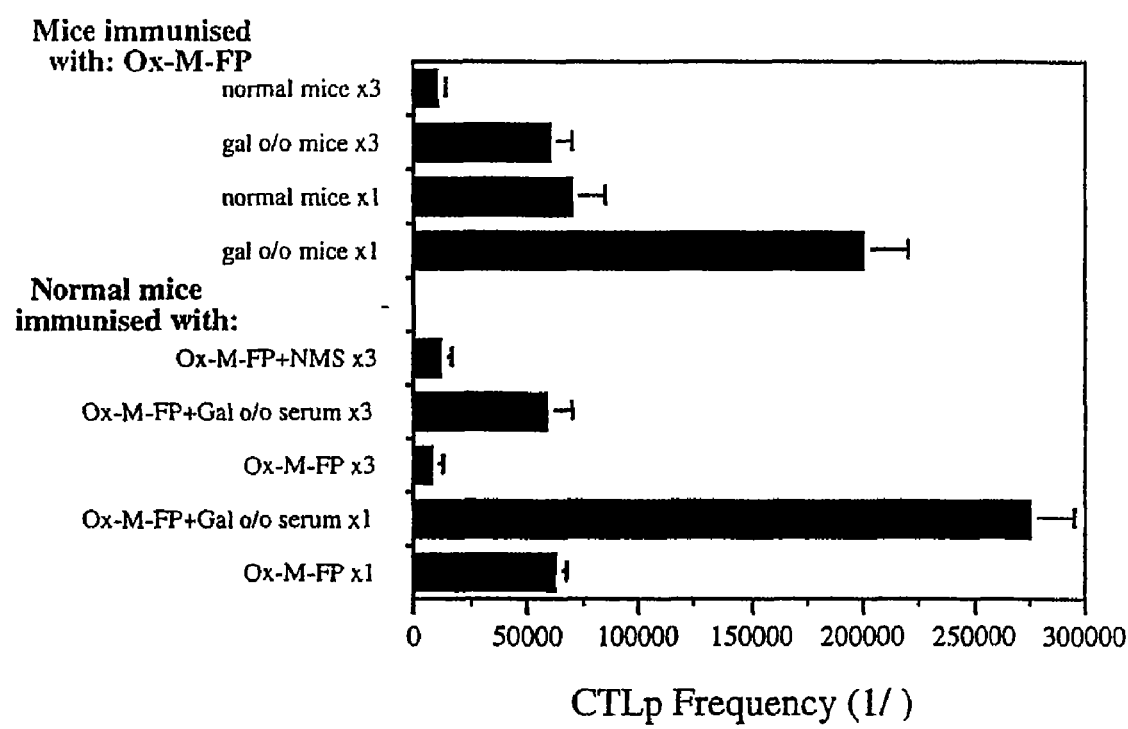
FIG. 11 illustrates the difference in CTLp frequencies between normal mice injected with ox-M-FP and ox-M-FP mixed with gal o/o serum.
Figure 12:
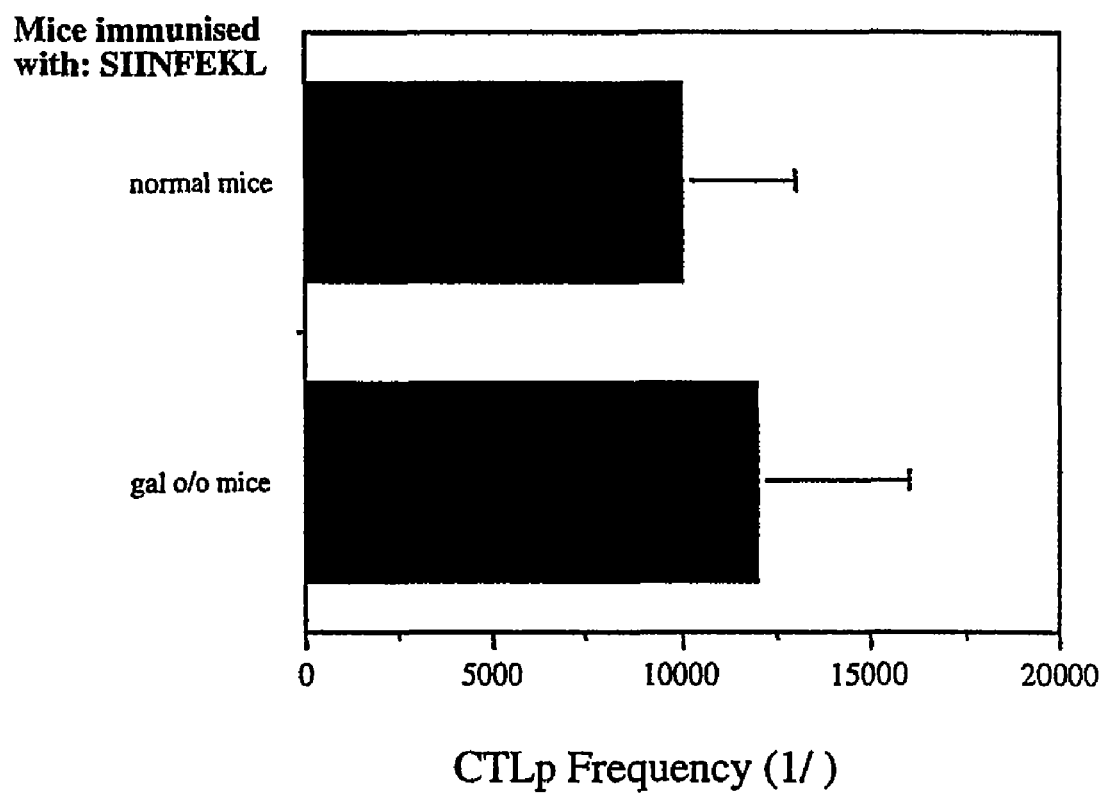
FIG. 12 illustrates the difference in CTLp frequencies between mice immunized with macrophage cells pulsed with ox-MSIINFEKL and mice immunized with macrophage cells pulsed with ox-M-SIINFEKL mixed with gal o/o serum.

Normal mice and gal o/o mice were injected with ox-M-FP and the resulting CTLp frequencies measured using methods generally described in Example 1. Referring to FIG. 11, either one or three injections of normal mice with ox-M-FP produced CTLp frequencies of 1/70,000 and 1/10,000, respectively. Similar injections into gal o/o mice resulted in CTLp frequencies of 1/200,000 (one injection) and 1/60,000 (three injections). Normal and gal o/o mice were also injected in a similar manner with a control peptide derived from ovalbumin. The difference in CTLp frequency in normal and gal o/o mice that was observed using ox-M-FP, was not observed using an ovalbumin epitope. Referring to FIG. 12, three immunizations of normal or gal o/o mice with mannan conjugated ovalbumin peptide gave CTLp frequencies of 1/10,000 and 1/12,000, respectively. Therefore, the reduced CTLp response in gal o/o mice was unique to MUC1 and gal o/o mice were capable of mounting CTLp responses to other antigens. The results indicated that CTLp frequency response to ox-M-FP immunization was greater in normal mice compared with gal o/o mice. These results are opposite to the antibody production results described above in Example 5. In a separate study, monkeys were immunized with ox-M-FP in a similar manner as the mice described immediately above. Referring to Table 5, monkeys immunized with ox-M-FP produced an antibody response, but not a CTLp response. This result is similar to that obtained using the gal o/o mice. Thus, in species in which CTLp can be measured, there is a correlation between the absence of pre-existing antibodies to galactose and the enhancement of CTLp responses by immunization with ox-M-FP.

Example 7

This example describes that antibodies to galactose reduce the appearance of CTLp when mixed with ox-M-FP prior to immunization of an animal.

Normal mice received either a single injection or three injections of either ox-M-FP or ox-M-FP mixed with gal o/o sera which contain anti-galactose antibodies. CTLp frequencies were obtained for the immunized mice using the methods generally described in Example 1. Referring to FIG. 11, mice that received a single injection gave a CTLp frequency of 1/62,000 when immunized with ox-M-FP and 1/275,000 when immunized with ox-M-FP mixed with gal o/o sera. Similarly, the CTLp frequencies for mice injected three times was 1/8,000 for ox-M-FP and 1/59,000 for ox-M-FP mixed with gal o/o sera. Thus, the addition of anti-galactose antibodies to ox-M-FP limited the generation of CTLp frequencies in normal mice to the level observed in gal o/o mice. In addition, injection of normal mice with ox-M-FP mixed with gal o/o serum led to significant antibody production (see Table 5).

Example 8

Figure 10:
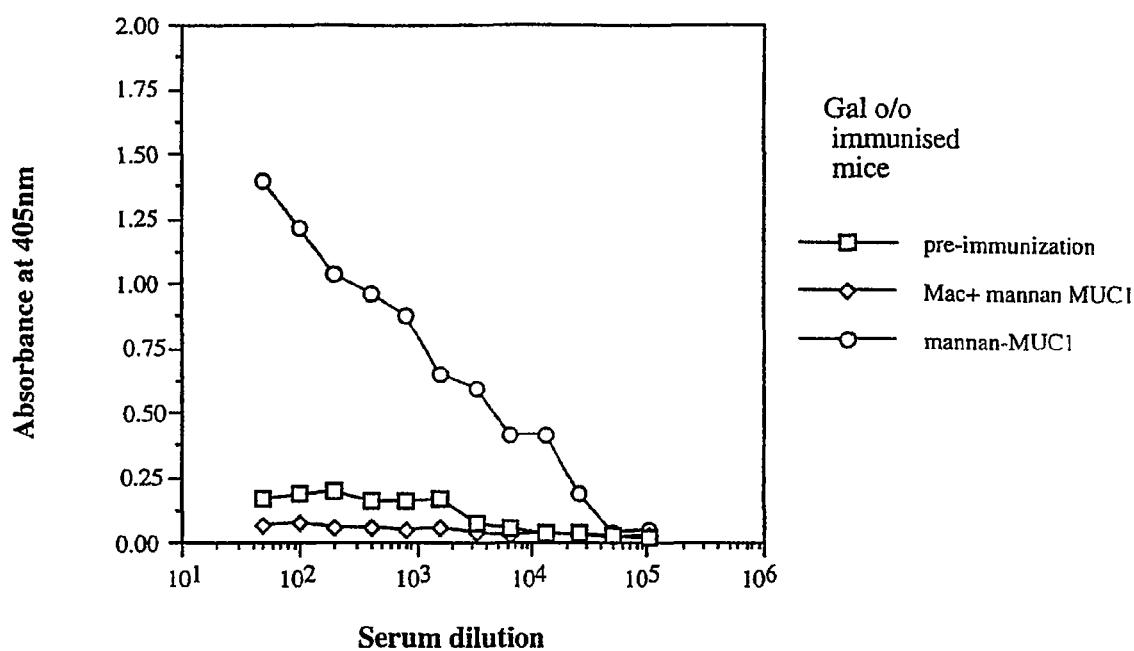
FIG. 10 illustrates the detection of anti-MUC1 peptide antibodies in serum isolated from Gal o/o mice immunized with either oxidized mannan fusion protein or macrophages pulsed with oxidized mannan fusion protein.
Figure 13:
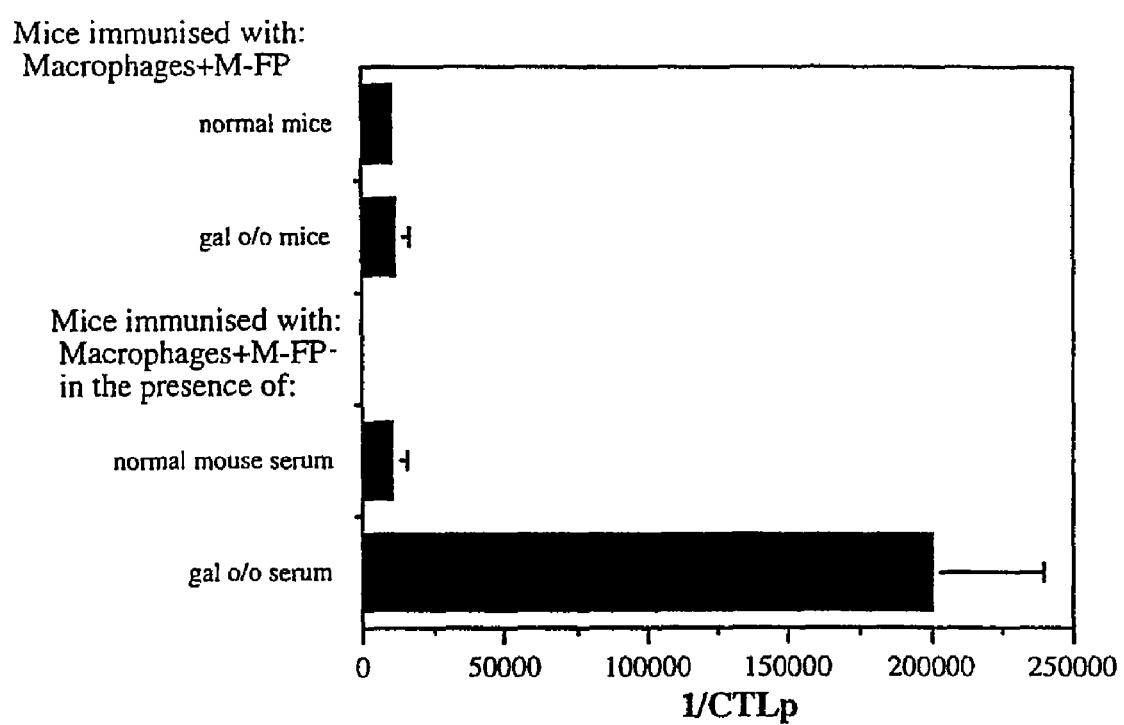
FIG. 13 illustrates the difference in CTLp frequencies between normal and Gal o/o mice immunized with macrophages and oxidized mannan fusion protein in the presence of either normal mouse serum or serum isolated from Gal o/o mice.

This example describes the immunization of normal and gal o/o mice with macrophage cells pulsed in vitro with ox-M-FP and the generation of CTLp, but not antibody, in such mice. Macrophage cells were obtained from C57BL/6 mice using the methods generally described in Example 1. The macrophage cells were pulsed overnight using either ox-M-FP or ox-M-FP mixed with gal o/o serum, using the methods generally described in Example 1. Normal and gal o/o mice were immunized with the pulsed macrophage cells using the methods generally described in Example 1. Referring to FIG. 13, immunization of gal o/o mice with the pulsed macrophages did elicit CTLp to a level essentially equivalent to normal mice (1/11,500 and 1/8,000, respectively), but did not elicit a detectable antibody response (see FIG. 10). Immunization of mice with macrophages pulsed with ox-M-FP mixed with gal o/o serum did not elicit a strong CTLp response.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

The invention claimed is:

1. An immunogenic composition comprising a conjugate between an antigen and an oxidized mannan comprising mannose units and aldehyde groups, and a pharmaceutically acceptable carrier.

2. The composition of claim 1 wherein the antigen is a tumor antigen.

3. The composition of claim 2 wherein the antigen comprises part of a fusion polypeptide.

4. The conjugate of claim 2 wherein the tumor antigen is selected from the group consisting of melanoma specific antigen, carcino embryonic antigen (CEA) from colon cancer, p53, Her2/neu, ErB2, melan A, MAGE antigens, nm23, BRACA1, and BRACA2.

5. The composition of claim 1, wherein the antigen is selected from the group consisting of pollens, hepatitis C virus (HIV) core, E1, E2 and NS2 proteins; *Plasmodium falciparum* circumsporozoite protein; HIV-gp120/160 envelope glycoprotein; streptococcus surface protein Ag; influenza nucleoprotein; hemagglutinin-neuraminidase surface infection; TcpA pilin subunit; VP1 protein; LMCV nucleoprotein; *Leishmania major* surface glycoprotein (gp63); *Bordetella pertussis* surface protein; rabies virus G protein; *Streptococcus* M protein; respiratory syncytial virus (RSV) F or G proteins; Epstein Barr virus (EBV) gp340 or nucleoantigen 3A, hemagglutinin, *Borrelia burgdorferi* outer surface protein (Osp) A, *Mycobacterium tuberculosis* 38 kDa lipoprotein or Ag85, *Neisseria meningitides* class 1 outer protein, *Varicella zoster* virus IE62 and gpI, *Rubella* virus capsid protein, Hepatitis B virus pre S1 ag, Herpes simplex virus type I glycoprotein G or gp D or CP27, Murray valley encephalitis virus E glycoprotein, Hepatitis A virus VP1, polio virus capsid protein VP1, VP2 and VP3, chlamydia trachomatis surface protein, Hepatitis B virus envelope Ag pre S2, Human rhinovirus (HRV) capsid, papillomavirus peptides from oncogene E6 and E7, *Listeria* surface protein, *Varicella* virus envelope protein, *Vaccinia* virus envelope protein, *Brucella* surface protein, and a combination of one or more of said antigens.

6. The composition of claim 1, wherein the antigen comprises whole cells or sub-cellular fractions thereof.

7. The composition of claim 6 wherein the whole cells or sub-cellular fractions thereof are, derived from tumor cells.

8. The conjugate of claim 7 wherein the tumor cells are selected from the group consisting of breast, lung, pancreas, colon and melanoma cells.

9. The composition of claim 4 or 5 wherein the antigen comprises part of a fusion polypeptide.

* * * * *